(12) United States Patent
Halpern et al.

(10) Patent No.: US 11,793,437 B2
(45) Date of Patent: Oct. 24, 2023

(54) NEURAL INTERFACE DEVICE AND INSERTION TOOLS

(71) Applicant: Modular Bionics Inc., Santa Ana, CA (US)

(72) Inventors: Ian Loren Halpern, San Francisco, CA (US); Mark William Merlo, Santa Ana, CA (US)

(73) Assignee: Modular Bionics Inc., Berkeley, CA (US)

( * ) Notice: Subject to any disclaimer, the term of this patent is extended or adjusted under 35 U.S.C. 154(b) by 1027 days.

(21) Appl. No.: 16/531,528

(22) Filed: Aug. 5, 2019

(65) Prior Publication Data

US 2020/0163565 A1 May 28, 2020

Related U.S. Application Data

(63) Continuation of application No. 14/814,388, filed on Jul. 30, 2015, now Pat. No. 10,368,761, which is a (Continued)

(51) Int. Cl.
*A61N 1/05* (2006.01)
*A61B 5/24* (2021.01)
(Continued)

(52) U.S. Cl.
CPC ............... *A61B 5/24* (2021.01); *A61B 5/291* (2021.01); *A61B 5/685* (2013.01); *A61N 1/0558* (2013.01);
(Continued)

(58) Field of Classification Search
CPC .......... A61B 5/24; A61B 5/291; A61B 5/685; A61B 2560/0219; A61B 2562/046;
(Continued)

(56) References Cited

U.S. PATENT DOCUMENTS

| 4,151,365 A | 2/1979 | Fischell et al. |
| 4,154,228 A | 5/1979 | Feldstein et al. |

(Continued)

FOREIGN PATENT DOCUMENTS

| EP | 1985579 | 10/2008 |
| WO | WO 2010/138228 | 12/2010 |
| WO | WO 2013/096873 | 6/2013 |

OTHER PUBLICATIONS

U.S. Appl. No. 15/192,905, filed Jun. 24, 2016, Halpern et al.
(Continued)

*Primary Examiner* — Carl H Layno
*Assistant Examiner* — Anh-Khoa N Dinh
(74) *Attorney, Agent, or Firm* — Knobbe, Martens, Olson & Bear, LLP

(57) ABSTRACT

An implanted neural micro interface device comprises microfilaments of various materials and forms embedded within a body. The microfilaments form interaction sites with surrounding neural tissue at their exit points from the implantable body. The body and filaments are configurable in a multitude of positions to provide increased engagement of a given neural tissue section as well as interaction and closed loop feedback between the microfilament sites. Such configurations allow for a range of recording, stimulating, and treatment modalities for the device within research and clinical settings.

20 Claims, 20 Drawing Sheets

Related U.S. Application Data continuation of application No. 13/725,732, filed on Dec. 21, 2012, now Pat. No. 9,095,267.

(60) Provisional application No. 61/634,683, filed on Mar. 5, 2012, provisional application No. 61/630,944, filed on Dec. 22, 2011.

(51) Int. Cl.
  *A61B 5/00* (2006.01)
  *A61B 5/291* (2021.01)

(52) U.S. Cl.
  CPC . *A61B 2560/0219* (2013.01); *A61B 2562/046* (2013.01); *A61N 1/0502* (2013.01); *A61N 1/0529* (2013.01); *A61N 1/0531* (2013.01)

(58) Field of Classification Search
  CPC ....... A61B 6/032; A61B 6/037; A61B 6/4417; A61B 6/025; A61B 6/035; A61B 6/0492; A61B 6/4085; A61B 6/4208; A61B 6/4258; A61B 6/4435; A61B 6/4233; A61B 8/4416; A61B 6/4028; A61B 6/4241; A61B 17/688; A61B 2562/164; A61B 2562/166; A61B 2562/222; A61B 5/6868; A61N 1/0558; A61N 1/0502; A61N 1/0531; A61N 1/0529
  See application file for complete search history.

(56) References Cited

U.S. PATENT DOCUMENTS

| | | | |
|---|---|---|---|
| 4,207,903 A | 6/1980 | O'Neill | |
| 4,213,465 A | 7/1980 | Renheim | |
| 4,441,498 A | 4/1984 | Nordling | |
| 4,461,304 A | 7/1984 | Kuperstein | |
| 4,573,481 A | 3/1986 | Bullara | |
| 4,640,983 A | 2/1987 | Comte | |
| 4,920,979 A | 5/1990 | Bullara | |
| 4,964,414 A | 10/1990 | Handa et al. | |
| 5,215,088 A | 6/1993 | Normann et al. | |
| 5,361,760 A * | 11/1994 | Normann ............... | A61B 5/685 607/116 |
| 5,645,586 A | 7/1997 | Meltzer | |
| 5,843,093 A * | 12/1998 | Howard, III ............. | A61N 1/05 600/377 |
| 5,938,689 A | 8/1999 | Fischell et al. | |
| 6,002,957 A | 12/1999 | Finneran | |
| 6,009,350 A | 12/1999 | Renken | |
| 6,135,968 A | 10/2000 | Braunstein | |
| 6,215,454 B1 | 4/2001 | Tran | |
| 6,304,785 B1 | 10/2001 | McCreery et al. | |
| 6,447,530 B1 | 9/2002 | Ostrovsky et al. | |
| 6,456,256 B1 | 9/2002 | Amundson et al. | |
| 6,560,479 B2 | 5/2003 | van Drongelen | |
| 6,705,900 B2 | 3/2004 | Sommer et al. | |
| 6,719,582 B1 | 4/2004 | Swanson | |
| 6,748,260 B2 | 6/2004 | Au et al. | |
| 6,829,498 B2 | 12/2004 | Kipke et al. | |
| 6,921,295 B2 | 7/2005 | Sommer et al. | |
| 6,924,773 B1 | 8/2005 | Paratte | |
| 6,965,794 B2 | 11/2005 | Brody | |
| 7,006,859 B1 * | 2/2006 | Osorio .................. | A61N 1/0531 607/116 |
| 7,010,356 B2 | 3/2006 | Jog et al. | |
| 7,149,578 B2 | 12/2006 | Edvardsson | |
| 7,162,310 B2 | 1/2007 | Doan | |
| 7,203,548 B2 | 4/2007 | Whitehurst et al. | |
| 7,212,851 B2 | 5/2007 | Donoghue et al. | |
| 7,299,089 B2 | 11/2007 | Wolf et al. | |
| 7,343,205 B1 | 3/2008 | Pianca et al. | |
| 7,460,904 B2 | 12/2008 | Deadwyler et al. | |
| 7,548,775 B2 | 6/2009 | Kipke et al. | |
| 7,551,951 B1 | 6/2009 | Osorio et al. | |
| 7,729,758 B2 | 6/2010 | Haller et al. | |
| 7,751,877 B2 | 7/2010 | Flaherty et al. | |
| 7,805,175 B2 | 9/2010 | Lin et al. | |
| 7,991,475 B1 | 8/2011 | Tang et al. | |
| 8,024,022 B2 | 9/2011 | Schulman et al. | |
| 8,027,735 B1 | 9/2011 | Tzivskos et al. | |
| 8,086,322 B2 | 12/2011 | Schouenborg | |
| 8,090,448 B2 | 1/2012 | Greenberg et al. | |
| 8,112,160 B2 | 2/2012 | Foster | |
| 8,160,696 B2 | 4/2012 | Bendett et al. | |
| 8,224,459 B1 | 7/2012 | Pianca et al. | |
| 8,255,061 B2 | 8/2012 | Perlin et al. | |
| 8,498,694 B2 | 7/2013 | McGuire, Jr. et al. | |
| 8,774,937 B2 | 7/2014 | Mercanzini et al. | |
| 8,958,868 B2 | 2/2015 | Ghovanloo et al. | |
| 9,095,267 B2 | 8/2015 | Halpern et al. | |
| 9,240,630 B2 | 1/2016 | Joshi | |
| 10,086,192 B2 | 10/2018 | Halpern et al. | |
| 10,368,761 B2 | 8/2019 | Halpern et al. | |
| 10,674,914 B1 | 6/2020 | Halpern et al. | |
| 10,874,847 B2 | 12/2020 | Halpern et al. | |
| 11,065,439 B1 | 7/2021 | Halpern et al. | |
| 2004/0082875 A1 | 4/2004 | Donoghue et al. | |
| 2004/0199235 A1 | 10/2004 | Younis | |
| 2005/0021117 A1 | 1/2005 | He et al. | |
| 2006/0089669 A1 * | 4/2006 | Schreiner ........... | A61B 17/0218 606/205 |
| 2006/0173263 A1 | 8/2006 | He et al. | |
| 2006/0178655 A1 | 8/2006 | Santini, Jr. et al. | |
| 2006/0276882 A1 | 12/2006 | Case et al. | |
| 2007/0191906 A1 | 8/2007 | Iyer et al. | |
| 2007/0228273 A1 | 10/2007 | Sun et al. | |
| 2007/0228276 A1 | 10/2007 | Makino et al. | |
| 2008/0044449 A1 | 2/2008 | McKay | |
| 2008/0177364 A1 | 7/2008 | Bolea et al. | |
| 2008/0249443 A1 | 10/2008 | Avitable et al. | |
| 2009/0099441 A1 | 4/2009 | Giszter et al. | |
| 2009/0112278 A1 | 4/2009 | Wingeier et al. | |
| 2009/0157141 A1 | 6/2009 | Chiao et al. | |
| 2009/0177144 A1 | 7/2009 | Masmanidis et al. | |
| 2010/0023021 A1 | 1/2010 | Flaherty | |
| 2010/0036379 A1 * | 2/2010 | Prakash ............. | A61B 18/1445 606/51 |
| 2010/0036458 A1 | 2/2010 | Duftner et al. | |
| 2010/0178810 A2 | 7/2010 | Aarts et al. | |
| 2010/0198281 A1 | 8/2010 | Chang et al. | |
| 2010/0292759 A1 | 11/2010 | Hahn et al. | |
| 2011/0144467 A1 | 6/2011 | Yao et al. | |
| 2011/0144639 A1 | 6/2011 | Govari | |
| 2011/0288619 A1 | 11/2011 | Pianca | |
| 2012/0083719 A1 | 4/2012 | Mishelevich | |
| 2012/0123289 A1 | 5/2012 | Sorenson et al. | |
| 2012/0203129 A1 | 8/2012 | Rennaker | |
| 2012/0277834 A1 | 11/2012 | Mercanzini et al. | |
| 2012/0302856 A1 | 11/2012 | Chang et al. | |
| 2013/0002519 A1 | 1/2013 | Camacho et al. | |
| 2013/0172717 A1 | 7/2013 | Halpern et al. | |
| 2013/0204317 A1 | 8/2013 | Sauter-Starace et al. | |
| 2014/0094674 A1 | 4/2014 | Nurmikko et al. | |
| 2014/0213891 A1 | 7/2014 | Gilgunn et al. | |
| 2015/0335883 A1 | 11/2015 | Halpern et al. | |
| 2015/0360030 A1 | 12/2015 | Cartledge et al. | |
| 2018/0008819 A1 | 1/2018 | Halpern et al. | |
| 2018/0296845 A1 | 10/2018 | Baumgartner et al. | |
| 2019/0240478 A1 | 8/2019 | Halpern et al. | |
| 2020/0375460 A1 | 12/2020 | Halpern et al. | |
| 2021/0146124 A1 | 5/2021 | Halpern et al. | |

OTHER PUBLICATIONS

U.S. Appl. No. 16/216,797, filed Dec. 11, 2018, Halpern et al.
Barna, James S., et al., "A New Multielectrode Array for the Simultaneous Recording of Field Potentials and Unit Activity", Electroencephalography and Clinical Neurophysiology 1981, 52: pp. 494-496.
International Search Report dated Apr. 4, 2013 for PCT App. No. PCT/US2012/071429 in 8 pages.

(56) References Cited

OTHER PUBLICATIONS

Jellema et al. "A slim needle-shaped multiwire microelectrode for intracerebral recording." J. Neurosci. Methods, 40 (1991) 203-209.

Karmos, George, et al., "A New Multielectrode for Chronic Recording of Intracortical Field Potentials in Cats", Physiology & Behavior, 1982, vol. 29, pp. 567-570.

Nicolelis, Miguel A.L., "Methods for Neural Ensemble Recordings", CRC Press LLC, 1999, pp. 5-12 in 10 pages.

Plexon Neurotechnology Research Systems, V-Probe Technical Guide 8, 16, 24 and 32 Channels (2013) in 14 pages.

Ulbert, Dr. Istvan, "Investigation of the evoked and spontaneous intracortical electrical activity with multielectrodes in humans", Semmelweis University Doctoral School, Neurosciences, Budapest, 2001, in 101 pages.

Ulbert, Istvan, "Multiple channel microelectrode system for human epilepsy research", IEEE, 2006, pp. 222-225.

Ulbert, Istvan, et al., "In vivo laminar electrophysiology co-registered with histology in the hippocampus of patients with temporal lobe epilepsy", Experimental Neurology, 187 (2004), pp. 310-318.

Ulbert, Istvan, et al., "Multiple microelectrode-recording system for human intracortical applications", Journal of Neuroscience Methods, 106 (2001) 69-79.

\* cited by examiner

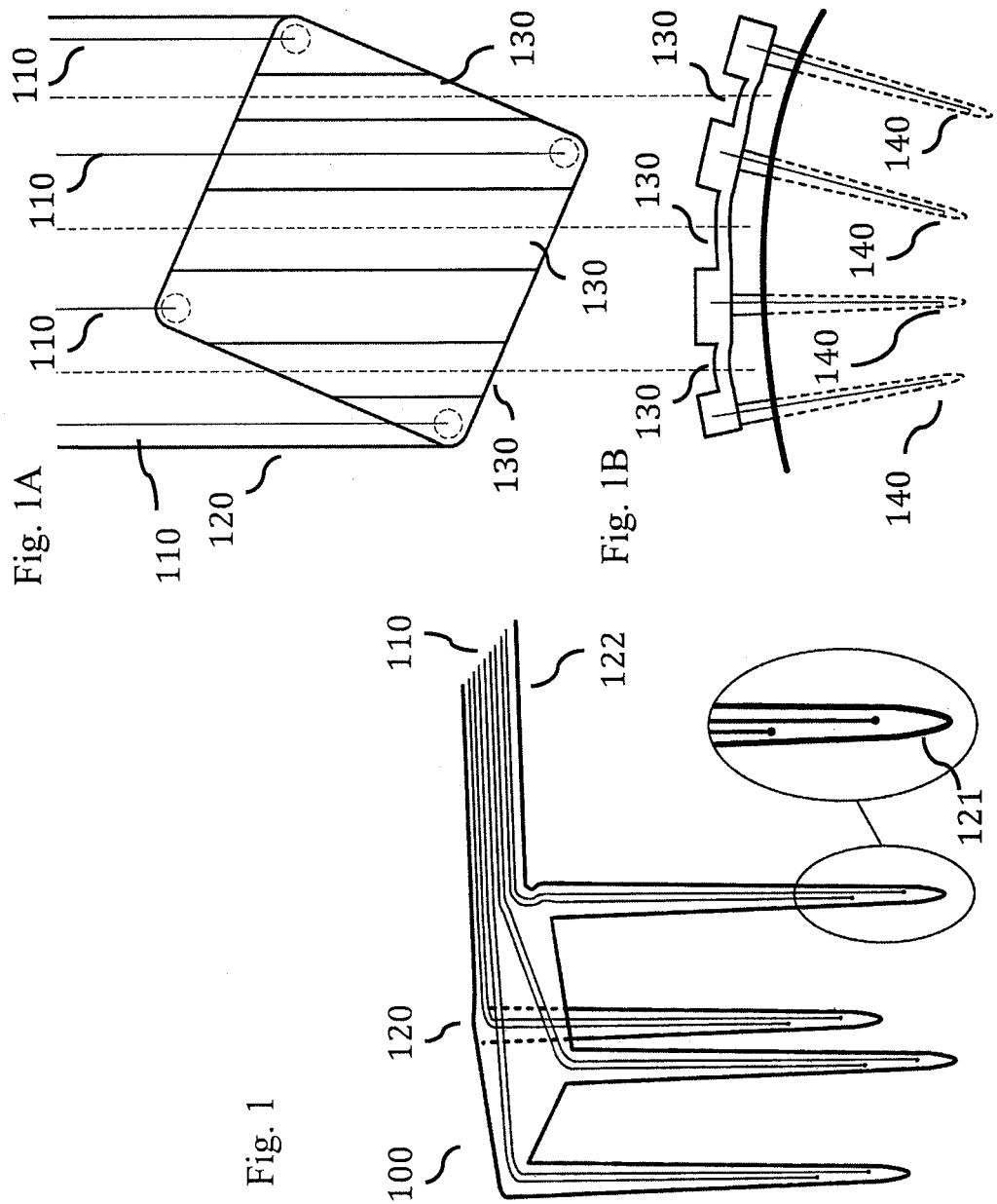

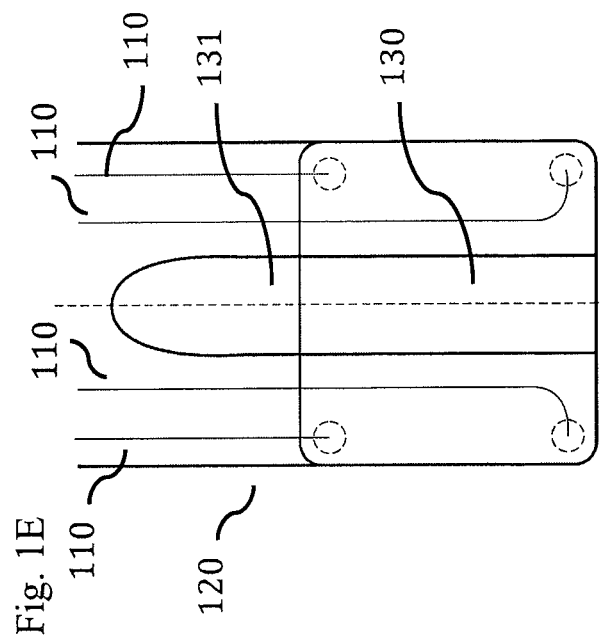
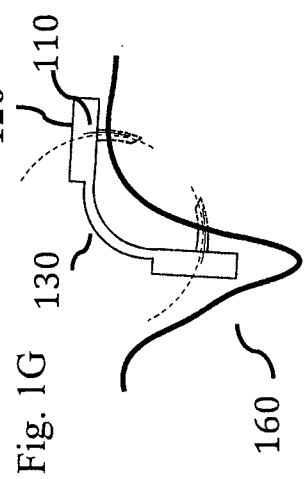
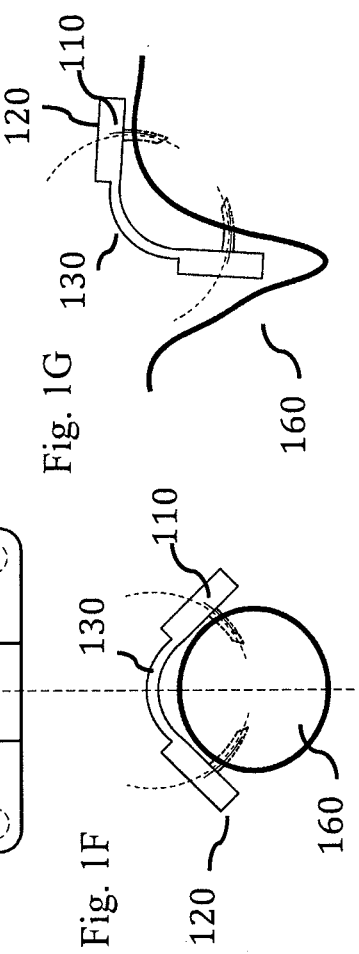

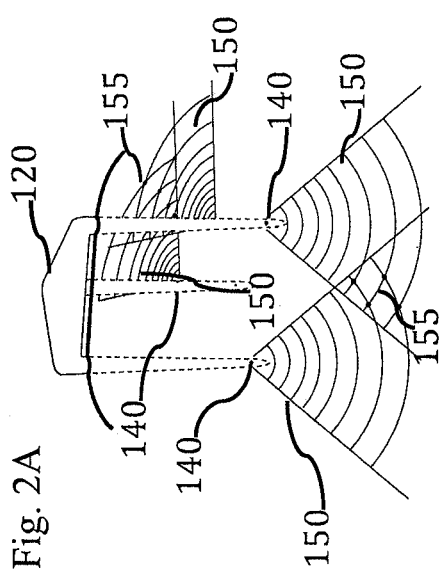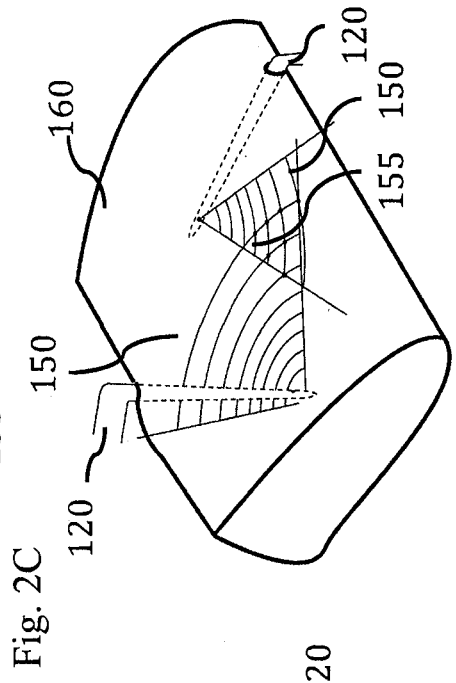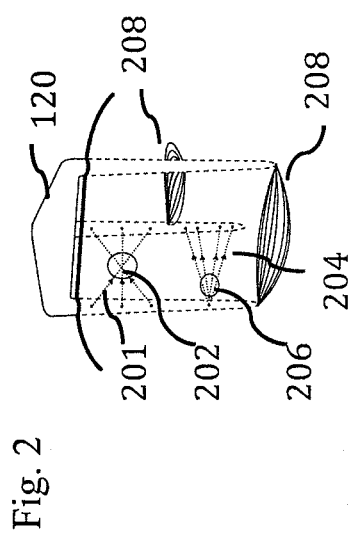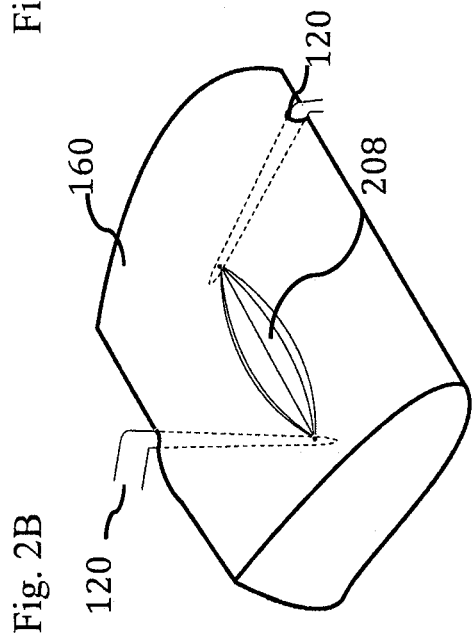
Fig. 2
Fig. 2A
Fig. 2B
Fig. 2C

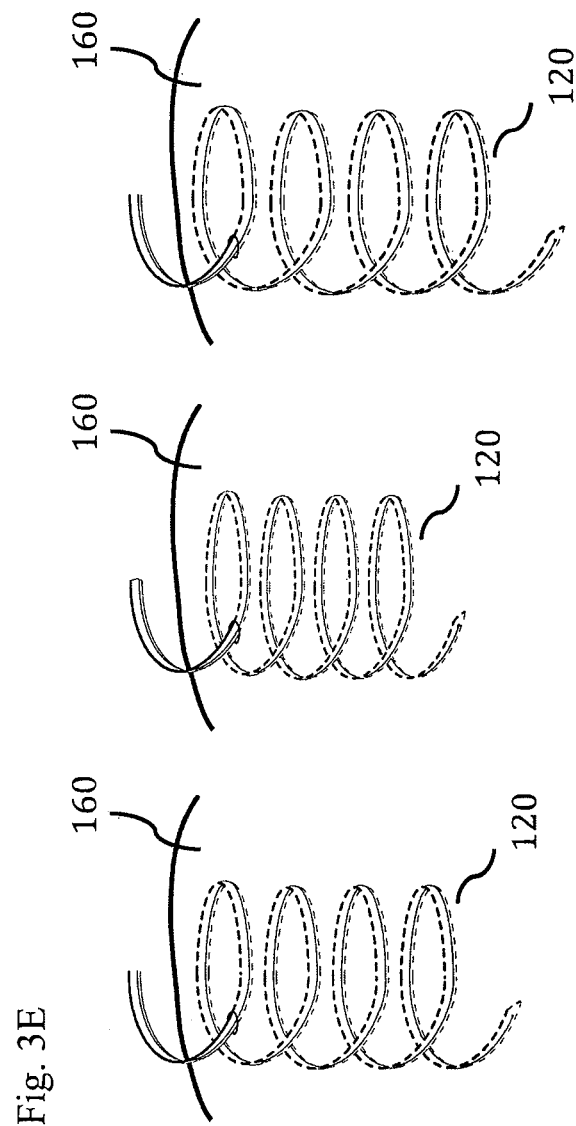

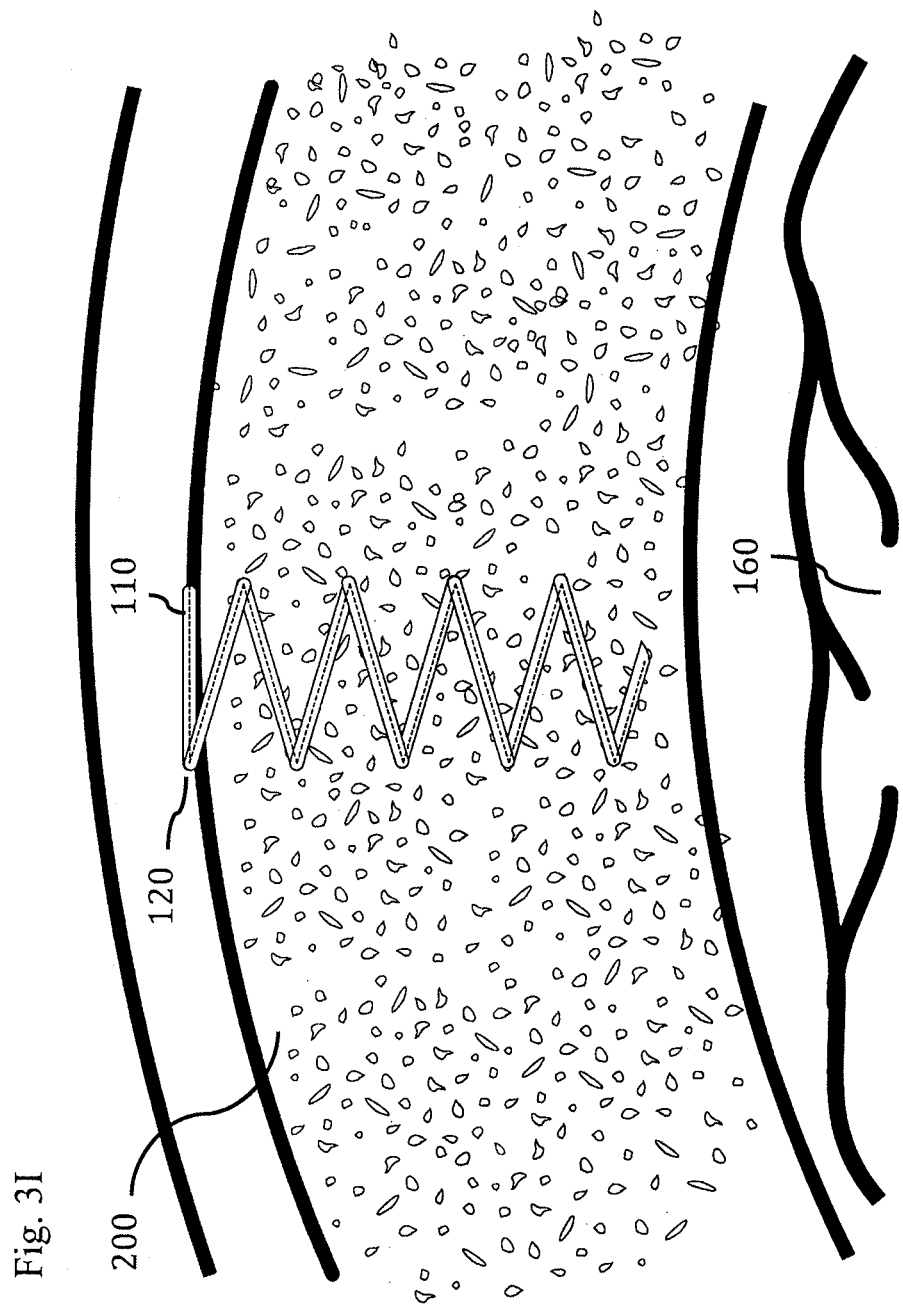

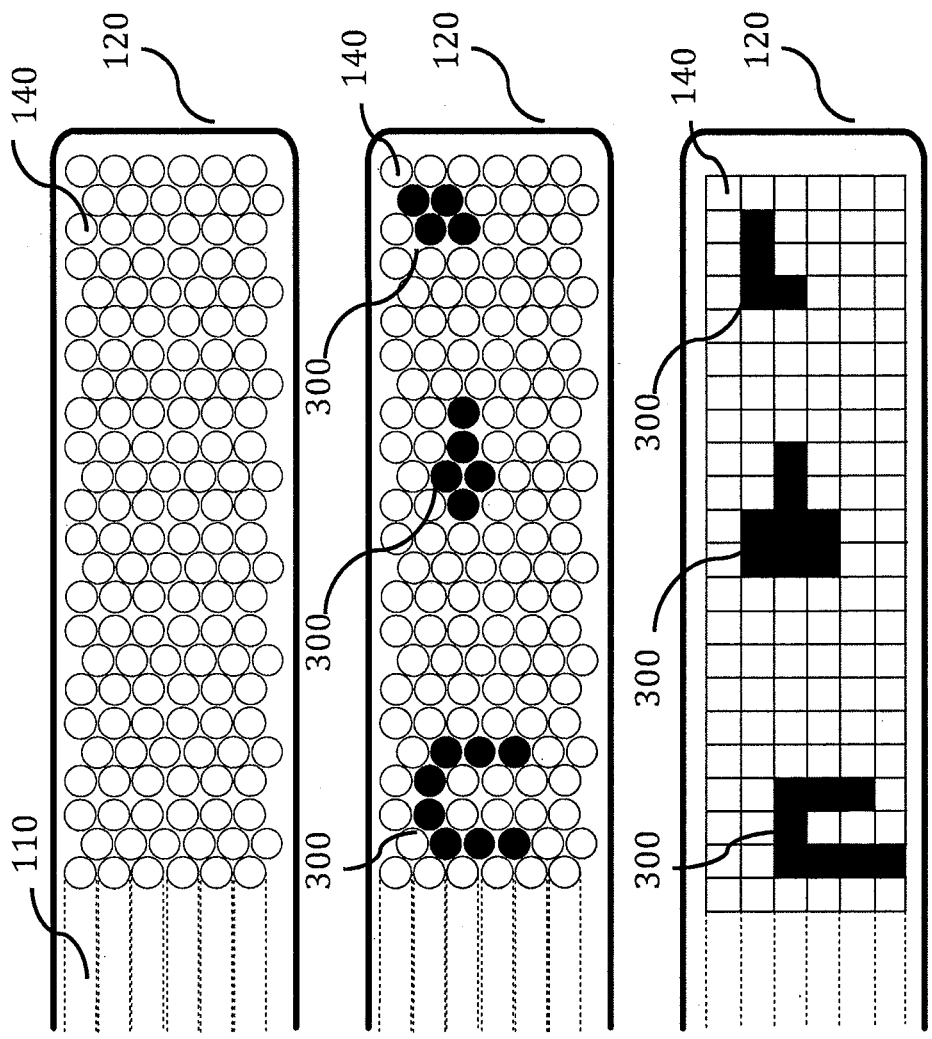

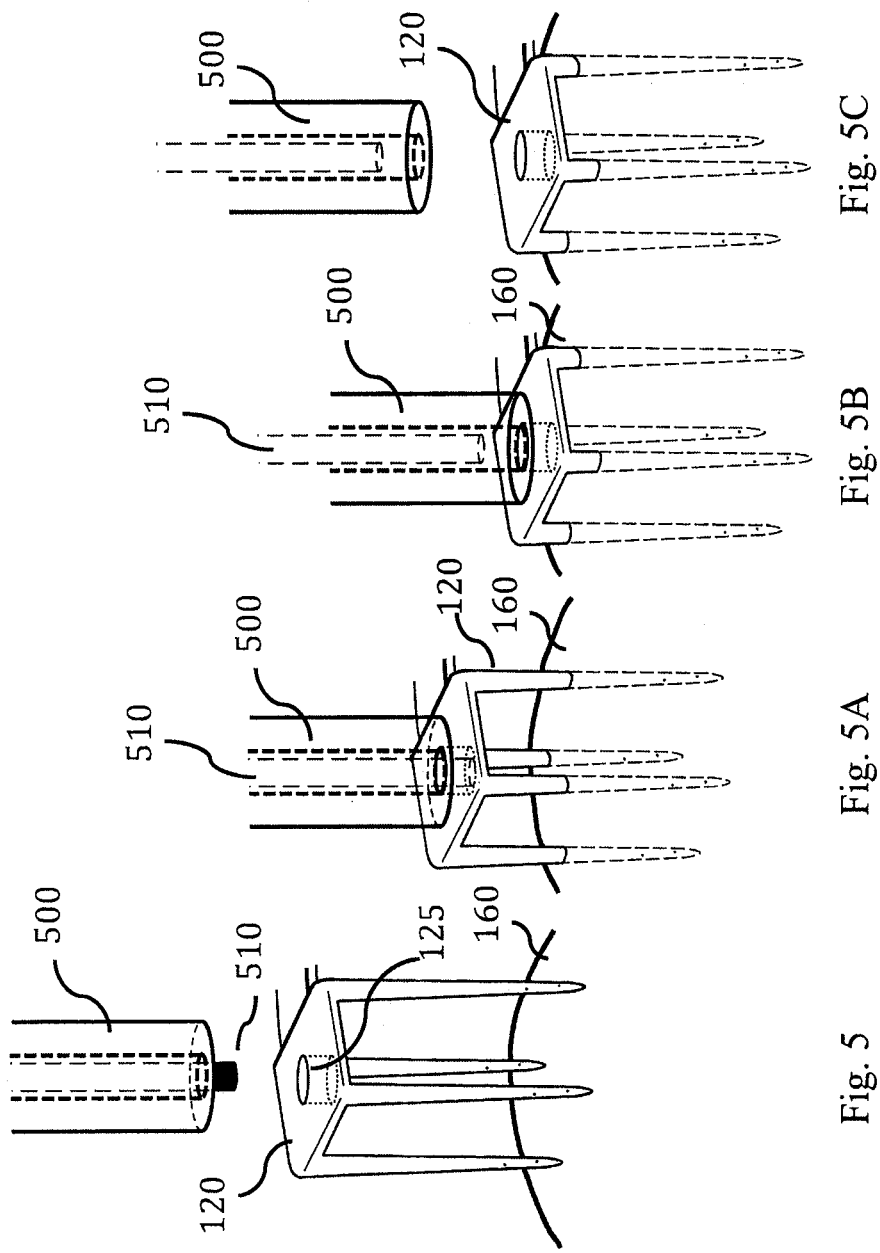

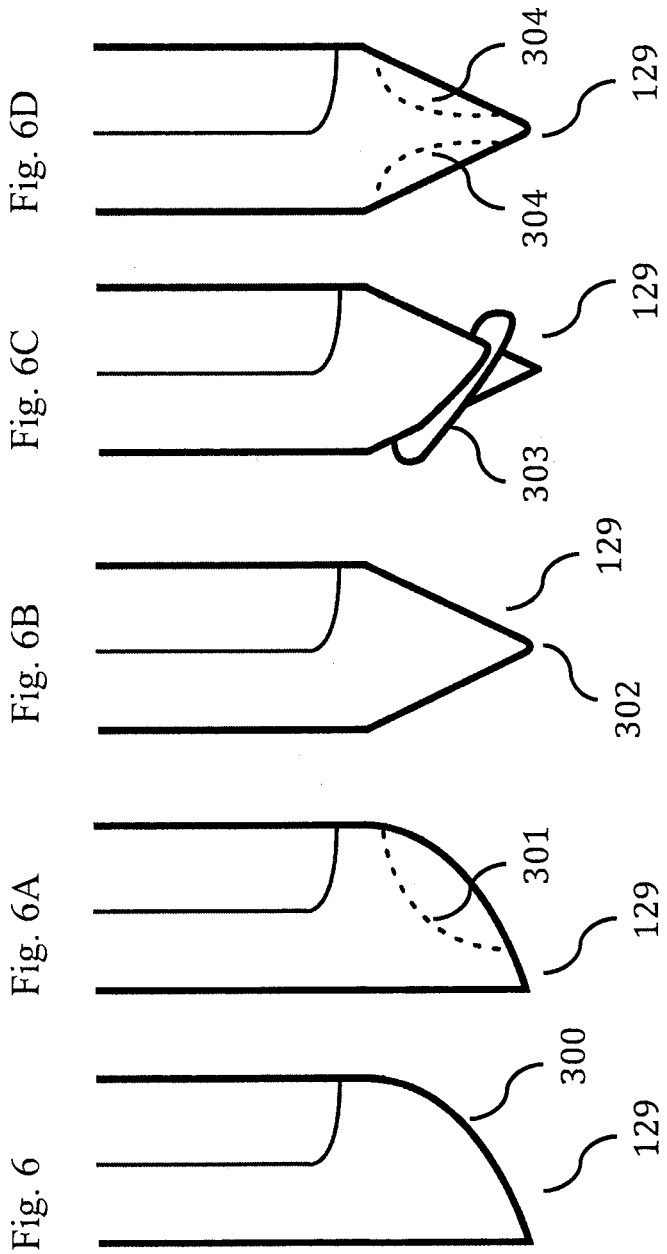

NEURAL INTERFACE DEVICE AND INSERTION TOOLS

CROSS-REFERENCE TO RELATED APPLICATIONS

The present application claims the benefit under 35 U.S.C. § 120 as a continuation application of U.S. patent application Ser. No. 14/814,388 filed on Jul. 30, 2015, now U.S. Pat. No. 10,368,761 B2, which in turn is a continuation application of U.S. patent application Ser. No. 13/725,732 filed on Dec. 21, 2012, now U.S. Pat. No. 9,095,267 B2, which in turn claims the benefit under 35 U.S.C. § 119(e) as a nonprovisional application of U.S. Prov. Pat. App. No. 61/630,944 filed on Dec. 22, 2011, and U.S. Prov. Pat. App. No. 61/634,683 filed on Mar. 5, 2012. Each of the aforementioned priority applications are hereby incorporated by reference in their entireties.

BACKGROUND

Disclosed herein are neural interface devices and tools used to implant and remove them within nervous systems. More particularly, the invention relates to, in some aspects, microelectrode, optogenetic, magnetic, and microfluidic array devices with control of recording, stimulating, and treating a volume of neural tissue and with a design that is easily configured and inserted into a variety of forms dependent upon the desired research or clinical purpose.

SUMMARY

In some embodiments, disclosed herein is a neural microarray. The microarray can include a base member, a plurality of elongate shafts extending from the base member, the elongate shafts each having a sidewall, a channel therethrough; and a plurality of sites in communication with the channel and spaced apart along the sidewall, the sites configured to stimulate tissue or record a tissue parameter; and a plurality of microfilaments housed within the channel of the plurality of elongate shafts and extending proximally from at least the base member and at least one of the microfilaments each extending distally out each of the plurality of sites. The base member could be flexible or rigid. The base member could include at least one, two, or more sites disposed on a surface, such as a tissue-facing surface of the base member. The sites can be configured such that the microfilaments are configured such that the microfilaments extend distally out of each of the plurality of sites and are configured to be movable in at least 1, 2, 3, 4, 5, 6, or more degrees of freedom when inserted in or proximate neural tissue. In some embodiments, the sites are spaced axially apart along longitudinal axes of the shafts. The shafts could comprise a helical shape, or a proximal non-linear portion and a distal linear portion. In some embodiments, the proximal non-linear portion is curved. The microarray could also include a power source operably connected to the microfilaments, and be connected via wires or wirelessly. The microarray could also include an amplifier operably connected to the microfilaments. The base member can have a major axis that is transverse to the major axis of the plurality of the elongate shafts, wherein a thickness dimension of the base member parallel to the major axis of the plurality of the elongate shafts is no more than about 1, 2, 3, 4, 5, 6, 7, 8, 9, 10, 15, 20, 25, or 30 times the average diameter of the plurality of microfilaments. In some embodiments, each shaft could have between about 2-12 sites, or between about 4-8 sites. In some embodiments, there could be between about 2-96 shafts extending from each base member, such as between 2-16 shafts per base member, or between about 2-48 shafts per base member.

Also disclosed herein is a method for modulating or monitoring neural activity, comprising: providing a microarray comprising a plurality of helically-shaped shafts comprising electrodes; inserting at least a portion of the helically-shaped shafts into neural tissue; and activating the electrodes to modulate or monitor neural activity. The method can also include providing an insertion tool comprising a distal zone operably connected to a proximal portion of the microarray; and disengaging the insertion tool from the microarray following the insertion step.

Also disclosed herein is a method for modulating neural activity, comprising: providing a microarray comprising a plurality of shafts comprising magnetic coils; inserting at least a portion of the shafts comprising the magnetic coils into neural tissue; and activating the magnetic coils sufficiently to modulate neural activity.

In some embodiments, disclosed is a method of modulating neural activity, comprising: providing a microarray comprising a first shaft and a second shaft, the first and second shaft each having a sidewall and at least one sidewall opening, the first and second shafts each comprising at least one conductive microfilament within a channel of the shafts such that a distal end of the microfilament is proximate the sidewall opening; inserting the first shaft within neural tissue such that the sidewall opening is within the neural tissue at a first location; inserting the second shaft at a second position within neural tissue such that the sidewall opening is within neural tissue at a second location; and activating the microfilaments, wherein following activation of the microfilaments, a constructive energy field effect is created within a zone of the neural tissue by the coordinating of the microfilaments. The microfilaments could be, for example, optically conductive, magnetic coils, electrically conductive, or a combination thereof, or having a stimulatory or recording function, or both. The first shaft and/or the second shaft could include a helical portion. Modulating neural activity can be achieved in a patient having, for example, a neurologic condition such as epilepsy, depression, or bipolar disorder for example.

Also disclosed herein is a method of modulating neural activity, comprising: providing a microarray comprising a first shaft and a second shaft, the first and second shaft each having a sidewall and at least one sidewall opening, the first and second shafts each comprising at least one conductive microfilament within a channel of the shafts such that a distal end of the microfilament is proximate the sidewall opening; inserting the first shaft within tissue such that the sidewall opening is within tissue at a first location; inserting the second shaft at a second position within tissue such that the sidewall opening is within tissue at a second location; and activating the microfilaments, wherein following activation of the microfilaments, a constructive energy field effect is created within a zone of target tissue by the coordinating of the microfilaments. The microfilaments could be in the target tissue or in the vicinity of the target tissue, or remote from the target tissue. In some embodiments, the microfilament sites could be within about 20 cm, 15 cm, 10 cm, 9 cm, 8 cm, 7 cm, 6 cm, 5 cm, 4 cm, 3 cm, 2 cm, 1 cm, 0.5 cm or less with respect to the target tissue. In some embodiments, the tissue is bone of the skull, and the target tissue is brain tissue. In some embodiments, the tissue and the target tissue both comprise neural tissue.

Also disclosed herein is a method for modulating neural activity, comprising: providing an elongate body having a proximal end, a distal end, a sidewall, a lumen at least partially therethrough, and at least one optical microfilament disposed within the lumen; inserting the elongate body into a first tissue; and activating the optical microfilament to direct light toward a second tissue remote from the first tissue, wherein the second tissue comprises neural tissue. The elongate body can include a coil shape, and in some cases substantially the entire elongate body comprises a coil shape. The first tissue could be bone, for example.

Also disclosed herein is a neural microarray, comprising a body portion; a plurality of microfilaments; and a microfilament controller, wherein the body portion is configured to house the plurality of microfilaments, wherein the plurality of microfilaments comprises a first subgroup of microfilaments, the first subgroup of microfilaments being configured to be activated simultaneously by the controller such that the microfilaments act in concert to function as a single electrode. The first subgroup of microfilaments can be electrically conductive, optically conductive, or comprise magnetic coils, or a combination thereof. Furthermore, the microarray can include a second subgroup of microfilaments, the second subgroup of microfilaments being configured to be activated simultaneously by the controller such that the microfilaments act in concert to function as a single electrode. The controller can be configured to dynamically increase or decrease the number of microfilaments in the first subgroup. The electrode could be a stimulating or recording electrode. The microfilaments could comprise a rectilinear, triangular, or other cross-section, or a combination of differing cross-sections. In some embodiments, a total area of non-conductive space between microfilaments within the body portion is less than about 20%, 15%, 10%, 5%, 3%, 2%, 1%, or less of the total area of the body portion for housing the microfilaments.

BRIEF DESCRIPTION OF THE DRAWINGS

FIG. 1 shows an isometric view of microfilaments embedded within a continuous body.

FIG. 1A shows a top view of microfilaments embedded within a continuous body.

FIG. 1B illustrates a side view of microfilaments embedded within a continuous body with recessed areas to provide flexing for conformity to curved surfaces.

FIG. 1E shows a top view of microfilaments 110 embedded within a continuous body with a central hinge section.

FIG. 1F shows the continuous body with non-linear penetrating sections placed in a circular section of tissue.

FIG. 1G shows the continuous body with non-linear penetrating sections placed in a recessed section of tissue.

FIG. 2 shows an isometric view of microfilaments embedded within a continuous body with microfilament end sites exposed to the outer environment near the end of the penetrating sections of the body. The sites are positioned and coordinated to create the desired current characteristic at areas of interaction within the penetrating sections, below the tips of the penetrating sections and outside of the penetrating sections.

FIG. 2A shows an isometric view of microfilaments embedded within a continuous body with microfilament end sites exposed to the outer environment near the end of the penetrating sections of the body. The sites are positioned and coordinated to create the desired light characteristic at areas of interaction within the penetrating sections, below the tips of the penetrating sections and outside of the penetrating sections.

FIG. 2B illustrates an isometric view of two continuous bodies with microfilaments embedded within them. These continuous bodies are positioned near one another within tissue so that the current generated at the microfilament end sites is coordinated to create the desired current characteristic at areas of interaction.

FIG. 2C illustrates an isometric view of two continuous bodies with microfilaments embedded within them. These continuous bodies are positioned near one another within tissue so that the light generated at the microfilament end sites is coordinated to create the desired light characteristic at areas of interaction.

FIG. 3E shows isometric views of a helical continuous body embedded with microfilaments illustrating its ability to compress and expand, when embedded in tissue.

FIG. 3I shows how a coiled continuous body with an embedded optical fiber microfilament placed within a section of bone generating light through a thin section of bone.

FIG. 4 shows a continuous body with embedded microfilaments arranged in a densely packed formation.

FIG. 4A shows a continuous body with embedded microfilaments arranged in a densely packed formation with three groups of microfilaments discharging current or light.

FIG. 4B shows microfilaments with rectilinear cross sections embedded within a continuous body to decrease gaps between microfilaments end sites.

FIG. 5 illustrates an insertion tool prior to engaging with a continuous body with embedded microfilaments.

FIG. 5A shows an insertion tool engaged with a continuous body with embedded microfilaments and driving it into tissue.

FIG. 5B shows an insertion tool withdrawing its engagement stem upon reaching full insertion.

FIG. 5C shows an insertion tool withdrawing after disengaging from the inserted continuous body with embedded microfilaments.

FIGS. 6-6D illustrates some embodiments of penetrating section tip geometry.

DETAILED DESCRIPTION

Figure 1C:
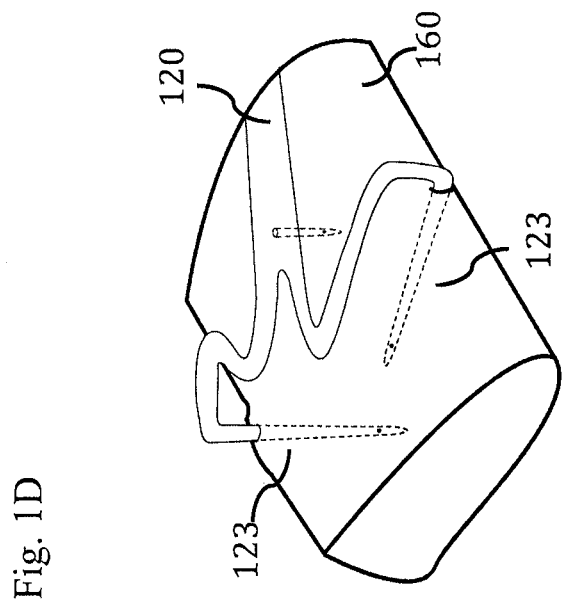
FIG. 1C shows an isometric view of microfilaments embedded within a continuous body including curved sections to provide custom placement of penetrating body sections within tissue.

Neural interfaces are implanted within the nervous systems of animals and humans to record, stimulate, and treat neural tissue activity. Typically, this occurs within animal research of a variety of fields (e.g. neurological disorders and basic nervous system function) as well as clinical diagnosis and therapy (e.g., epilepsy). While generally described herein in the context of neural interfaces, any of the embodiments herein can be used or adapted for use with a variety of neural as well as non-neural organs, tissues, and other anatomical locations.

Neural interfaces can include a variety of materials and structures. The lithographic multichannel shank electrode and its variations have found wide spread use in establishing a neural interface. These electrodes are most commonly formed using planar, lithographic processes and have been fabricated in a number of materials including silicon, glass, metal, ceramic and polymers. Conductive channels are lithographically layered within insulators to form multiple recording and stimulation sites on a rectangular shank for implantation into neural tissue. Stacking multiple planar electrodes together has demonstrated three-dimensional electrodes to provide greater recording or stimulation coverage of a given section of neural tissue. There are other electrode designs, such as the thinly coated silicon arrays consisting of approximately one hundred electrode sites located at the individual tips of linear penetrating shanks joined by a rigid backplate. The tips are inserted into neural tissue to record or stimulate neural activity. Simple microwire electrodes also exist. These have an individual, or family of microwires with only their tips exposed (the remainder is surrounded by an insulating coating); as with the previously mentioned coated silicon arrays, the tips are inserted into neural tissue to record or stimulate neural activity.

The amount of neural activity recorded, stimulated, or treated corresponds to the number and positioning of neural interface device sites for recording, stimulation, or fluid delivery within a given neural volume. Researchers and clinicians position neural interface devices carefully due to the limited number and configuration of sites available to them on a single micro scale interface (e.g., microelectrode array).

Unfortunately many current micro neural implants are poorly constructed for high density recording, stimulating, or treating of neural tissue volumes. For example, due to the limitations of their linear based construction and structures, existing microelectrodes are constrained in the positioning of sites, their proximity and angle to one another, and the end suitability of the device shape for implantation into neural tissue. These limitations prevent the increase of data acquired as well as current and future therapies. Current microelectrode designs are also limited in controlling the cross sectional shape of penetrating bodies irrelevant of the number of electrode sites and capabilities. In some embodiments, minimizing the cross sectional thickness reduces the adverse response of the body to neural implants.

Accordingly, in some embodiments, disclosed herein is a tissue interface, such as a neural interface, that provides six degrees of freedom for placement of microfilament sites (e.g., electrode, light emitting, magnetic coils, and fluid delivery sites) within an array as well as options for the structure and shape of its overall shape to optimize neural implantation. In some embodiments, the sites may be located either on the distal tip, or along the sidewall of one or more of the shafts, such as spaced apart at regular or irregular intervals. It can also be advantageous to minimize the body containing the microfilaments. By minimizing the body containing the microfilaments both within and adjacent neural tissue, the neural interface device can have greater conformity to anatomy and reduces body response during chronic (e.g., in some embodiments, the electrodes can be implanted for greater than one day, one week, one month, three months, six months, one year, 60 years, or more). In some embodiments, the neural interface is composed of only the body and microfilaments; the microfilaments act as structural elements to provide the desired mechanical characteristics. In some embodiments, the microfilaments exit the baseplate proximally within a conduit operably connected to a power source, connector, or control circuitry. In other embodiments, the microfilaments terminate proximally within the baseplate at a wireless power terminal, connector, or control circuitry (not shown). Wireless power can be supplied by, for example, inductive charging. In some embodiments, the baseplate has the approximate width to thickness ratio of 4 to 1, or at least about 4 to 1, 5 to 1, 8 to 1, 10 to 1, or more.

A flexible baseplate (e.g., joining body) is also advantageous in some embodiments as it allows researchers and surgeons customization of placement within the nervous system and increased conformity to anatomical variations. In some embodiments, the joining body is configured to be flexible enough to bend around the outer curvature of neural tissue (e.g., sulcus surface of cortex, circumference of a nerve, or surface of a plexus). In some embodiments the joining body is configured to be flexible enough to bend with the motion of neural tissue due to respiration or containing body acceleration and deceleration. The ability to shape the tip geometry of penetrating sections and form a penetrating section into a helical form reduces the insertion force required for insertion of a probe, and thus a reduction in the probe's required cross sectional area can also be advantageous in some cases. In some embodiments, the body has sections of relatively decreased thickness with respect to other sections, or sections that are more flexible than other sections to further bend and conform to the target anatomy.

In some embodiments, disclosed herein is an implantable neural interface device. The body of the device has various types of embedded microfilaments that act as recording or stimulation electrodes, optical fibers, or as hollow tubes for media, e.g., fluid delivery. The body of the device and its penetrating surfaces can be shaped into advantageous configurations for implantation, site density, site interaction, and various treatment modalities including recording, stimulating, magnetic stimulation, magnetic monitoring, fluid delivery, temperature control, optical stimulation, optical monitoring, and chemical irrigation of neural tissue. In some embodiments, the body containing the microfilaments is coated with a drug, such as an antithrombotic agent, an antibiotic, an anti-inflammatory, an anti-epileptic, or a chemotherapeutic agent, for example. In some embodiments, the implantable neural interface device can be placed within any tissue within the body dependent upon the desired research or clinical result; including nervous, muscle, connective, epithelial, cardiac, lung, renal, gastrointestinal, and bone tissues. In some embodiments, the implantable neural interface device can be used to diagnosis and/or treat epilepsy, a movement disorder (e.g., Parkinson's Disease), a psychiatric disorder (e.g., clinical depression), the result of a stroke, Alzheimer's disease, a cognitive disorder, an anxiety disorder, an eating disorder, an addition or craving, restless leg syndrome, a sleep disorder, Tourette's syndrome, a stress disorder, coma, autism, a hearing disorder, a vision disorder, retinal degeneration, age related macular degeneration, dry eye syndrome, a speech disorder, amblyopia, headaches, temporomandibular joint disorder, pain (e.g., phantom limb pain and acute or chronic pain) such as sciatica, urinary or fecal incontinence, sexual dysfunction including erectile dysfunction, bone disease including osteoporosis or fractures, arthritis, tendinitis, the result of ligament or tendon damage, and paralysis (e.g., facial nerve paralysis and spinal paralysis). In some embodiments, the implantable neural interface device can be used to provide control of a prosthetic such as a limb or an external computer.

In some embodiments, systems and methods as disclosed herein can modulate neural tissue, and have a stimulatory or inhibitory effect. Neural tissue is specialized for the conduction of electrical impulses that convey information or instructions from one region of the body to another. About 98% of neural tissue is concentrated in the brain and spinal cord, which are the control centers for the nervous system. Neurons transmit signals as electrical charges which affect their cell membranes. A neuron has a cell body (soma) that contains a nucleus. The stimulus that results in the production of an electrical impulse usually affects the cell membrane of one of the dendrites, which then eventually travels along the length of an axon, which can be a meter long. Axons are often called nerve fibers with each ending at a synaptic terminal. Neuroglia are cells of the CNS (central nervous system) and PNS (peripheral nervous system) that support and protect the neurons. They provide the physical support for neural tissue by forming myelin sheaths, as well as maintaining the chemical composition of the tissue fluids and defending the tissue from infection. Schwann cells are specialized PNS cells that form myelin sheaths around neurons. Neurons (nerve cell) include a cell body that contains the nucleus and regulates the functioning of the neuron. Neurons also include axons which are cellular process (extension) that carry impulses away from the cell body. Neurons also include dendrites which are cellular process (extension) that carry impulses toward the cell body. A synapse is a space between axon of one neuron and the dendrite or cell body of the next neuron—transmits impulses from one neuron to the others. Neurotransmitters are chemicals released by axons and transmit impulses across synapses.

In certain coiled configurations, the conductive embedded microfilaments can also generate magnetic fields. Once in an implanted position within neural tissue, a current run through a coiled conductive microfilament generates a magnetic stimulation of a targeted volume of neural tissue. In addition to stimulating neural tissue, the magnetic field could be used to inhibit neural activity by blocking the typical mechanisms of neural communication. The transmission of a magnetic field into neural tissue can also be achieved by placing the coiled microfilament in close proximity to neural tissue (e.g., within bone such as the cranium). These magnetic fields can range between 0.1 µT-0.01 T. The magnetic field can alternate in a variety of waveforms with the maximum strength ranging between 0.1 µT to 2 T, such as no more than about 0.1 mT, 1 mT, 10 mT, or 100 mT. The coiled microfilaments can also be used to monitor magnetic fields that are, for example, generated by the neural interface device or by an external source. In addition to stimulating neural tissue, the magnetic field could be used for other purposes, such as inhibiting neural activity by blocking the typical mechanisms of neural communication.

In some embodiments, provided is a closed loop control system for stimulating and monitoring neural activity. To meet this objective, microfilaments are embedded in various body configurations with six degrees of freedom to provide many system options for interacting with neural tissue. As an example, this would enable the data collected from a first recording microfilament (or external source) to help guide the output of a second stimulating microfilament dynamically and on-the-fly.

The approximate diameter of circular microfilaments for conducting electrical current is between 1 µm and 250 µm, such as no more than about 25 µm, 50 µm, or 75 µm. For electrical stimulation, larger sites up to 50 µm would be advantageous to achieve surface areas that meet useful stimulation current requirements without a coating. The approximate diameter of circular microfilaments for conducting or monitoring light is between is 0.1 µm to 250 µm, such as no more than about 25 µm, 50 µm, or 75 µm. The approximate diameter of circular microfilament tubes for delivering or circulating gases, fluids, and mixtures in some embodiments is between 1 µm to 100 µm, or no more than about 50 µm, 75 µm, 100 µm, or 150 µm. Microfilaments can also be placed within a packed geometry that allows for a tapering of the penetrating area cross sections to reduce the cross sectional area and thus long term adverse neural tissue response. In some embodiments, the microfilaments can extend outward from the body's surface; these sites can be formed (e.g., bent or flattened) to provide desired functional characteristics.

The array body can take multiple forms including penetrating structures with microfilament sites and joining sections to optimize placement within the nervous system. An approximate cross sectional area of a penetrating array body in some embodiments is 1 µm$^2$ to 0.2 µmm$^2$, preferably up to approximately 7850 µm$^2$. For large area coverage as in electrocorticography, larger body areas up to approximately 100 cm$^2$ or more could be advantageous to collect more data from the outer surface of a neural tissue section.

The array body can also take on a substantially helical shape that allows a novel insertion technique of screwing, e.g., circumferentially, into neural tissue. This requires a lower insertion force than a linear body shape and provides a more advantageous angle of attack. Some neural implantation surgeries involve significant motion (e.g., due to respiration), a helical shape is capable of absorbing this motion while being rotated into position. The lower insertion force required of the helical inserter provides an opportunity for increased control during the insertion procedure. Once inserted, the helical form can also flex with neural tissue with a tuned spring coefficient as well as bend and flex near the point of entry as with a typical electrode. The helical form can be between 0.1 µmm and 20 µmm in length with a 1.0 µm$^2$ to 0.2 µmm$^2$, in some cases up to approximately 7850 µm$^2$ or more cross sectional area with a variety of shapes to further reduce insertion force and tissue damage (e.g. a tapering cross section).

The array body can also take on non linear shapes, which allow novel insertion techniques into difficult areas to access within surgery. A curved shape can be rotated into position where a linear angle of attack is unavailable. The array body can also have one, two, or more curves located at different positions (e.g., proximal, midportion, or distal) to aid in anchoring to neural tissue or bone, while there may be a linear segment distal to, and/or proximal to the curved segment.

One advantage of the device in some embodiments is the wide range of materials and components available for the microfilaments and body to improve insertion conditions and long term performance within a nervous system. The microfilaments can be formed from gold, platinum, platinum iridium, carbon, stainless steel, steel, aluminum, conductive polymers, polymers, organic materials or any other material known to those skilled in the state of the art. The body can be formed from polymers, metals, composites, organic materials, or any other material known to those skilled in the state of the art. Another advantage of the device in some embodiments is the ability to combine within a volume of neural tissue many different interface types (e.g., electrodes with optical fibers with fluid delivery); this provides a novel approach to research and clinical treatment within a single body. Yet another advantage of the device in some embodiments is the many shapes possible with the microfilament containing body. The shape of the body can be customized for a given procedure, area of anatomy, and functional purpose. An example of an advantageous form is a substantially coiled shape that utilizes a conductive filament to produce a magnetic field for neural stimulation. The coiled shape also has the advantage of a lower insertion force, as well as compression or extension after implantation to more closely move with the surrounding neural tissue. Yet another advantage in some embodiments is the placement of coiled conductive microfilaments within a penetrating body. Positioning of the coiled conductive microfilaments and current selected will generate magnetic fields of varying characteristics within neural tissue; this has advantageous effects including the blocking of tissue electrical activity or stimulation. A three-dimensional view of an example of a neural interface device 100 is shown in FIG. 1. In general, two distinct parts of the device can be distinguished: microfilaments 110 and a body, such as a continuous body 120 surrounding the microfilaments. Microfilaments in some embodiments can be conductive materials that transmit current. In some embodiments, microfilaments can be optical fibers that transmit or monitor light. In still other embodiments, microfilaments can be hollow tubes that transport fluids and mixtures. In some embodiments, a device 100 could include a combination of one, two, or more of conductive, optical, or hollow tube microfilaments or others. In some embodiments the continuous body 120 includes penetrating structures. The continuous body 120 can be a single material from the penetrating tips 121 to the end of its flexible cable 122, e.g., integrally formed. The continuous body can have areas as thin as, or even thinner than the microfilament 110. In some embodiments, the continuous body could be integrally formed, or formed as part of a plurality of bodies joined together, so long as it is physically continuously connected together as a whole.

FIG. 1A illustrates a plurality of microfilaments 110 embedded within the continuous body 120. The top view shows the orientation of microfilaments 110 to provide space for one, two, or more movable walls, e.g., hinged sections 130 with wall thicknesses between 0.5 µm and 1000 µm in some embodiments to provide flexibility. The baseplate 120 could have a first section having a first thickness, and a second section having a second thickness that is more or less than the first thickness.

FIG. 1B illustrates a side view of microfilaments 110 embedded within the continuous body 120. In some embodiments, the microfilaments can be molded or otherwise fixed in place and exit the continuous body at an exit port or opening in the body and have a distal end that can be flush with the continuous body outer surface at sites 140. In some embodiments, the site need not include a physical opening, for example for an optical fiber that terminates within a site configured to radiate or monitor light through the baseplate and/or shaft (e.g., an optically transparent area). In other words, the site 140 can be configured with or without a physical opening, but just be configured to transmit energy or monitor a parameter.

Conductive microfilament sites 140 are capable of recording or stimulating electrical activity nearby within tissue. Optical fiber microfilament sites are capable of stimulating neural activity utilizing optogenetic techniques (i.e. transfection of tissue to respond to exposure to a specific form of light). Microfilaments can also form tips of penetrating sections 123 of continuous body 120.

Figure 1D:
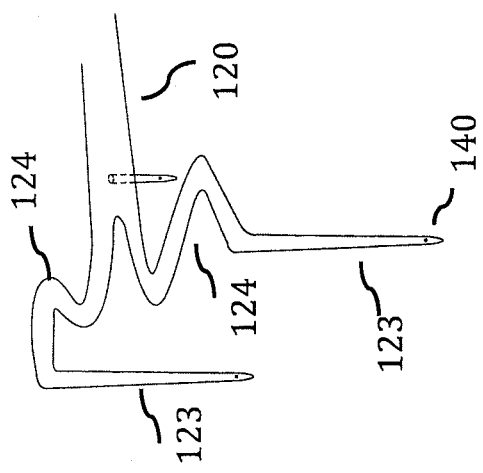
FIG. 1D illustrates an isometric view of microfilaments embedded within a continuous body with its curved sections flexed to provide desired entry points for the body's penetrating sections.

FIG. 1C illustrates another embodiment of microfilaments 110 embedded within a continuous body 120 with curved sections 124 ending in penetrating sections (that could be linear as illustrated) 123 to provide flexibility. The curved sections 124 can be straightened (e.g., temporarily) or malleable to provide multiple options for placing the penetrating sections 123. FIG. 1D shows the penetrating sections 123 of a continuous body 120 placed within a section of tissue 160.

In some embodiments, the continuous body has one, two, or more shaped voids in desired locations to increase the continuous body's ability to collapse, fold, form, or otherwise shape itself to a targeted area of tissue. In some embodiments, the shaped voids can be used in conjunction with flexible or movable sections to increase the continuous body's capability to fold or collapse within six degrees of freedom and better fit the wide variety of target tissue shapes. For example, a body could have a first section that is more flexible than a second section, or first and second sections connected by a third section that is more flexible than the first and second sections.

FIG. 1E illustrates another embodiment of microfilaments 110 embedded within a continuous body 120 with a hinge, joint, or otherwise movable section 130 with wall thickness between 0.5 μm and 1000 μm in some cases. The hinge could be, for example, a fold, living hinge or a mechanical-type hinge. The section 131 can be, for example, a void in the continuous body 120 that allows both the continuous body 120 and the movable section 130 to have greater flexibility. FIG. 1F shows the continuous body 120 with non-linear penetrating sections rotated to penetrate a circular section of tissue 160. FIG. 1G shows non-linear penetrating sections rotated to penetrate a depression within a section of tissue 160 (e.g., sulcus of the cortex).

Figure 2D:
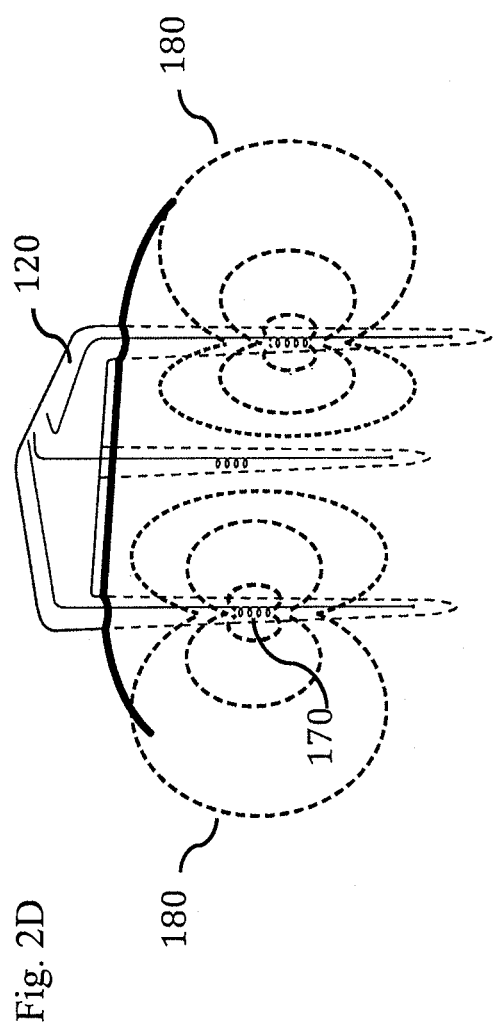
FIG. 2D shows an isometric view of microfilaments embedded within a continuous body with conductive microfilaments coiled within each penetrating section before terminating in electrode sites.
Figure 2E:
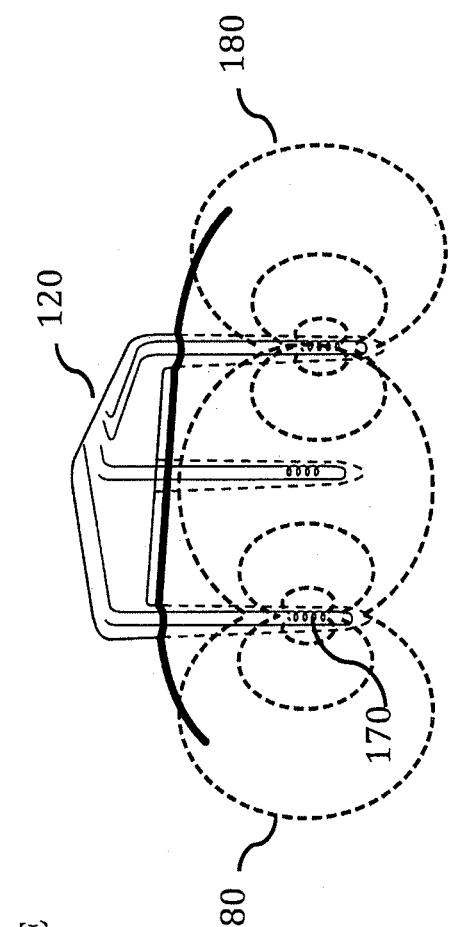
FIG. 2E shows an isometric view of microfilaments embedded within a continuous body with conductive microfilaments coiled within each penetrating section and routed back into the joining area of the continuous body. Current passed through the conductive coiled microfilaments generates magnetic fields. These magnetic fields influence one another and are tuned to generate desired magnetic stimulation of neural tissue within the volume of tissue near the penetrating sections.
Figure 2F:
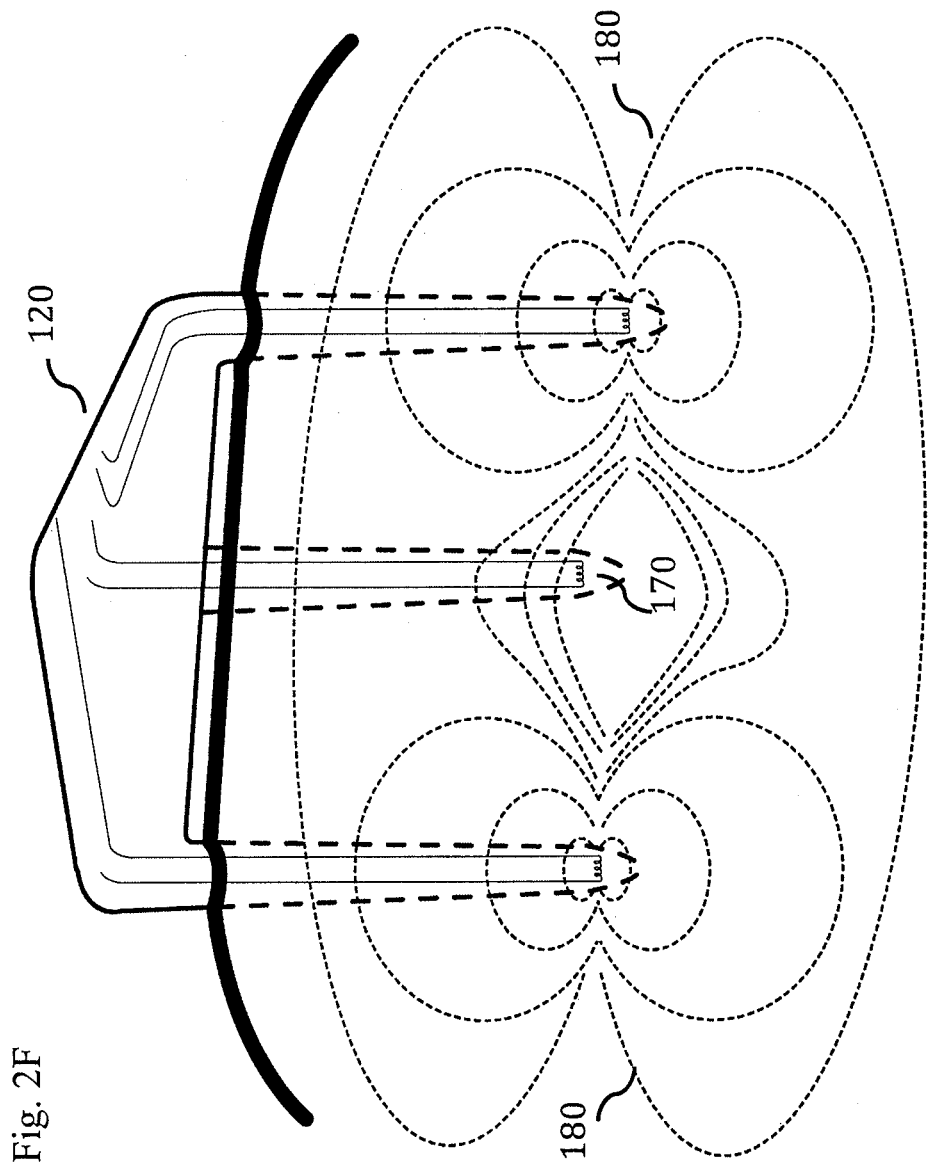
FIG. 2F shows an isometric view of microfilaments embedded within a continuous body with conductive microfilaments coiled within each penetrating section and routed back into the joining area of the continuous body. Current passed through the conductive coiled microfilaments generates magnetic fields. These magnetic fields influence one another and are tuned to generate desired magnetic stimulation of neural tissue within the volume of tissue near the penetrating sections.
Figure 2G:
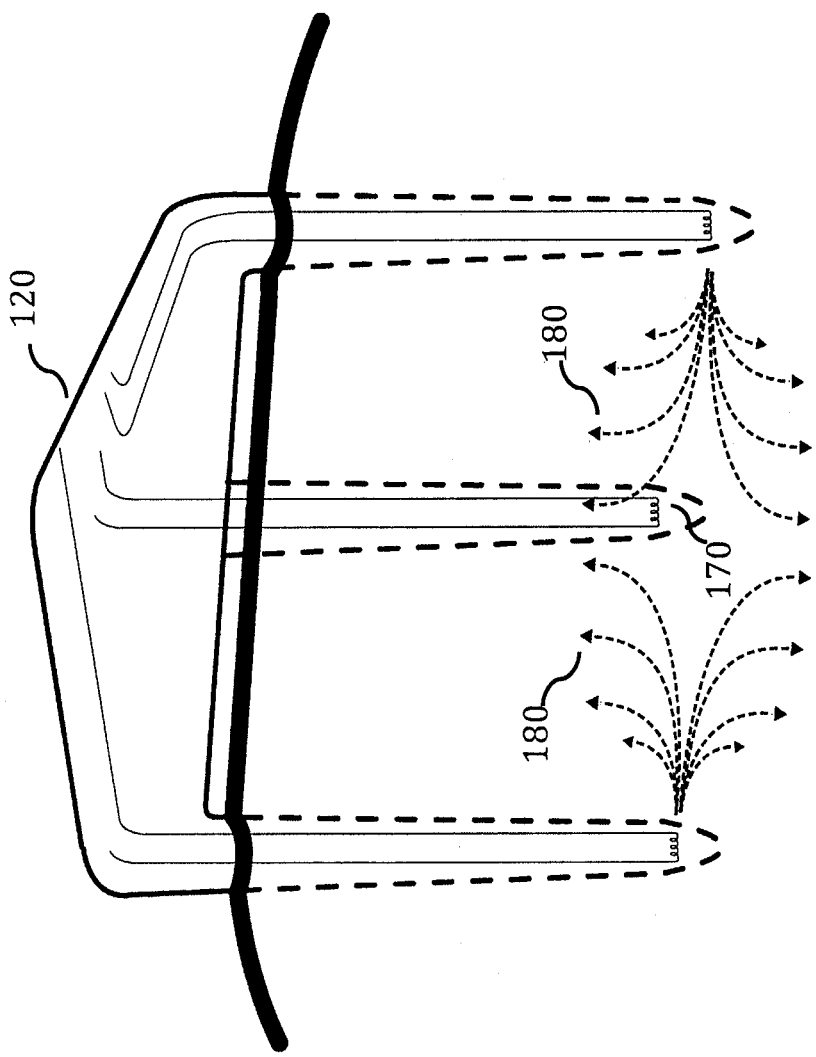
FIG. 2G shows an isometric view of microfilaments embedded within a continuous body with conductive microfilaments coiled within each penetrating section and routed back into the joining area of the continuous body. Current passed through the conductive coiled microfilaments generates magnetic fields. These magnetic fields influence one another and are tuned to generate desired magnetic stimulation of neural tissue within the volume of tissue near the penetrating sections.
Figure 2H:
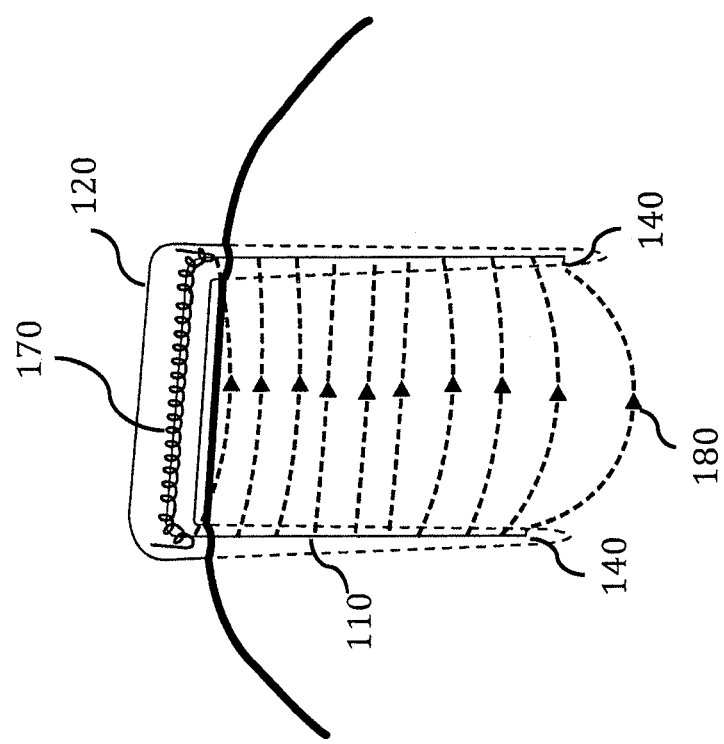
FIG. 2H shows an isometric view of conductive microfilaments embedded within a continuous body. A magnetically conductive microfilament terminating within each penetrating section of the continuous body is surrounded by a second coiled conductive microfilament. Current passed through the coiled filament generates a magnetic field between magnetically conductive microfilament. A magnetic field is also generated at the ends of the coiled microfilament. These magnetic fields can be tuned independently or with influence upon one another to generate desired magnetic stimulation of neural tissue within the volume of tissue near the penetrating sections.

FIGS. 2-2H are schematic diagrams showing how different embodiments of microfilament sites 140 can interact with each other within an array to illustrate using one or multiple types of microfilaments in an array that interacts with itself. FIG. 2 shows a continuous body 120 with a plurality of, e.g., three shafts having penetrating sections and microfilament sites 140. The microfilament sites 140 are positioned and coordinated relative to one another so that they interact at specific areas. Microfilaments formed from different or the same materials can be used within the same continuous body 120.

In some embodiments, microfilament sites 140 form current source and sink pairs as indicated by lines 201. The microfilament site pairs can be activated at different times such that the cumulative charge within region 202 reaches a threshold to cause stimulation, while the charge outside region 202 remains below activation threshold. Multiple methods exist for activating the sink/source pairs including a linearly sequential scan, a scan to reduce adjacent interactions, or an interleaving bipolar stimulation scheme with all of the cathodic pulses occurring before the anodic pulses for example.

In some embodiments, a microfilament site 140 acts as a current source (or sink) while multiple sites 140 act as a current sink (or source). Lines 204 display this one-to-many (e.g., more than one, two, three, four, or more) pairing between sites 140. This could also be extended to a few-to-many pairing (e.g., two-to-five, three-to-three, three-to-ten, or any other combination). This configuration generates activation region 206 in the area of larger charge concentration.

The sites 140 could be on the distal end of a given shaft, and/or on the sidewalls of a given shaft. In some embodiments, each shaft could have 2, 3, 4, 5, 6, 7, 8, 9, 10, or more sites each regularly or irregularly spaced apart axially along the longitudinal axis of the shaft, or along a curved length of a shaft for non-linear embodiments. In some embodiments, a first shaft could have the same number, more, or less sites than a second shaft. Each site could have the same or different attributes, e.g., a first site that is electrically active, a second site that is optically active, a third site that is magnetically active. Some sites could function as stimulatory sites, while other sites could function as recording sites.

In some embodiments, two (or more) sites flow charge 208 between each other. The tissue within high charge region 208 activates the corresponding tissue, which could exist within, outside, or below the penetrating body.

In some embodiments, the microfilament sites 140 configured to stimulate or record tissue parameters are located in the body itself 120 (e.g., one, two, or more sites 140 residing on a surface, such as a distal-facing surface of the baseplate, which can have a major axis that is generally parallel to the target tissue surface in some embodiments) and interact through the surface of the tissue with the penetrating bodies or other surface located sites 140. In all of these methods, an external electrode (not shown) could be used to collect any unbalanced charge.

FIG. 2A shows waves of energy, such as light 150 generated by microfilament sites 140 interfering with one another within areas 155. In other words, activation of a first microfilament site can create a first energy zone, and activation of a second microfilament site spaced apart from the first microfilament site can create a second energy zone. An interference zone (either constructive or destructive) can be created where the first energy zone and the second energy zone intersect. In some embodiments, the energy, e.g., light intensity increases at intersections of constructive interference within areas 155. In some embodiments, the areas of light interference 155 can be used to increase the light intensity beyond the threshold required to modulate transfected tissue using optogenetic techniques. As such, a more focused area of constructive interference 155 can be created by the intersection of two or more beams 150, focusing the treatment of tissue within that area. Combining different wavelengths (e.g., colors) of light generated at sites 140 can create desired wavelength combination (e.g., colors) within areas of light interference 155. Areas of light interference 155 are controllable volumes of tissue modulation dependent upon the intensity of the light sources, wavelength of light sources, positioning of microfilament sites 140, focal characteristics of light sources, and frequency of light generation. In some embodiments, the microfilament sites 140 can also be positioned within the joining section of continuous body 120 to provide additional options for areas of light interferences 155. FIG. 2B shows the use of first and second continuous bodies 120 spaced apart and positioned relative to one another so that their respective microfilament sites 140 create a charge region 208 within a section of neural tissue 160. FIG. 2C shows the use of two continuous bodies 120 positioned relative to one another so that their microfilament sites 140 create an additive light area of interaction 155 within a section of neural tissue 160.

FIGS. 2D-2G illustrate the use of coiled microfilaments 170 within continuous bodies 120 to generate magnetic fields 180 that stimulate neural tissue. Dependent upon the positioning of the coiled microfilaments 170 within the continuous body 120, the magnetic fields 180 interact with one another in different areas. FIG. 2H illustrates a magnetically conductive microfilament 110 within a continuous body 120 that is encircled by a coiled microfilament 170. A current passing through microfilament 170 emits a first magnetic field 180 as well as generating an additional second magnetic field 180 between microfilament 110.

In some embodiments, the continuous body 120 is in a coiled form (e.g., a helix). A coiled continuous body provides a number of possible advantages, including six degrees of freedom for the placement of microfilament sites 140, as described in additional detail herein.

Figure 3A:
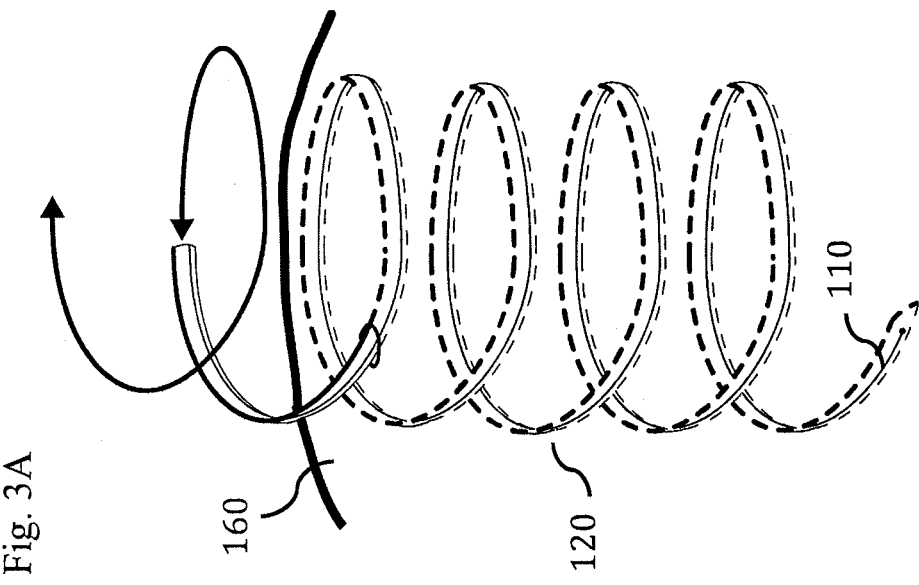
FIG. 3A shows an isometric view of a microfilament within a continuous body of a coiled shape rotated into tissue 160.
Figure 3:
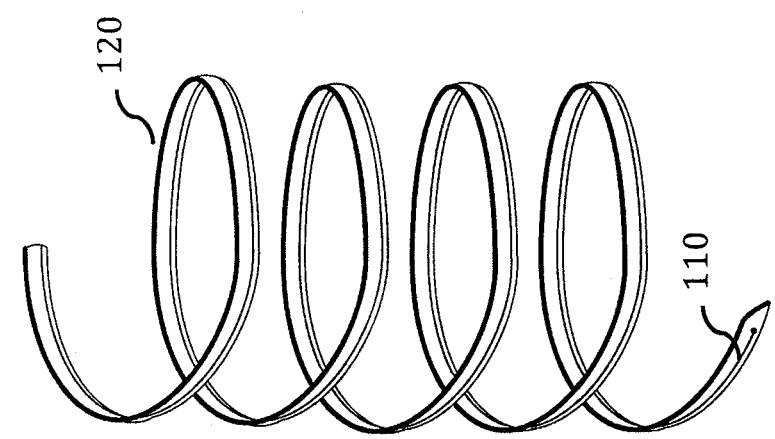
FIG. 3 shows an isometric view of a microfilament within a continuous body of a coiled shape.

FIG. 3 shows an isometric view of a microfilament 110 within a continuous body 120 of a coiled shape. FIG. 3A shows an isometric view of a microfilament 110 within a continuous body 120 of a coiled shape rotated into tissue 160.

Figure 3B:
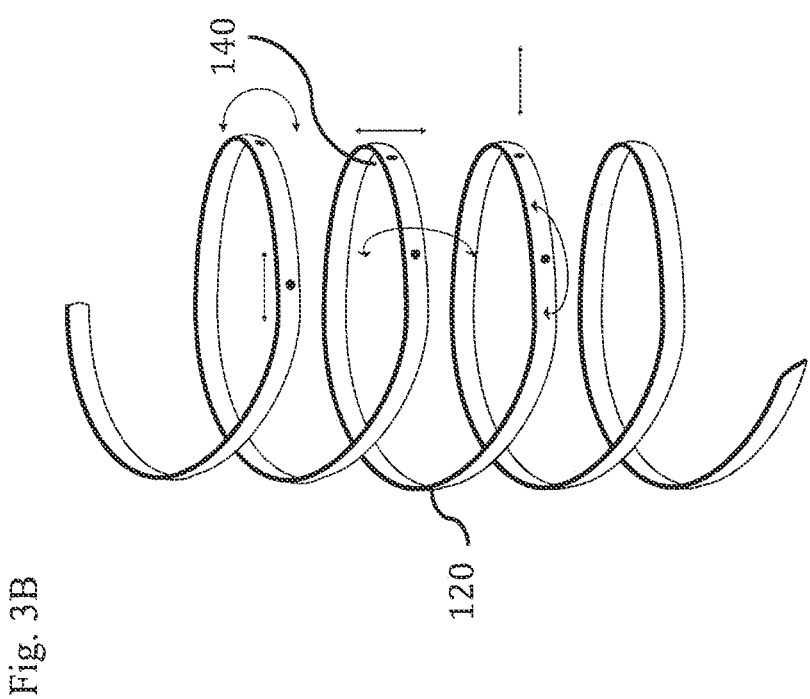
FIG. 3B shows an isometric view of microfilaments within a continuous body of a coiled shape. The six degrees of freedom of the microfilament end sites are illustrated.
Figure 3D:
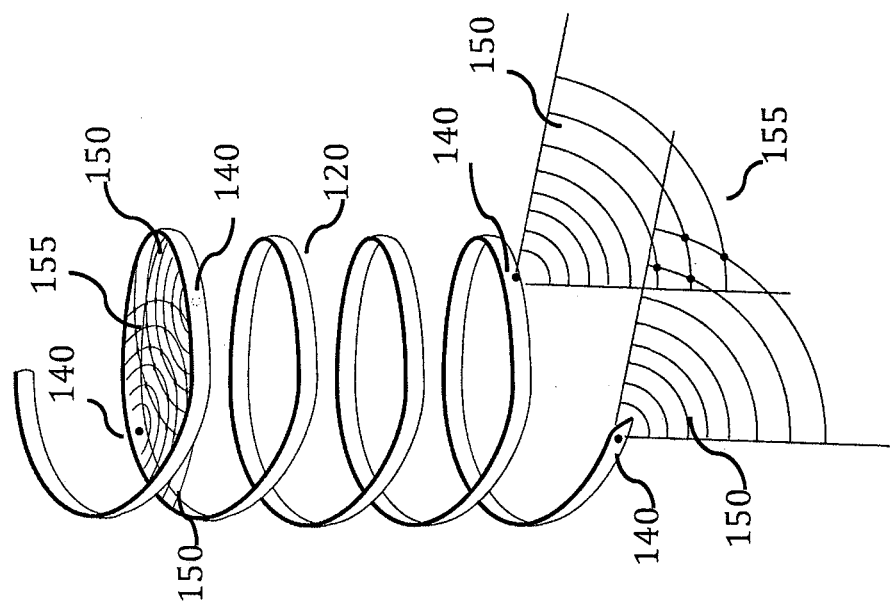
FIG. 3D shows an isometric view of microfilaments within a continuous body of a coiled shape with the end sites of the microfilaments positioned and coordinated to create the desired light characteristic at points of interaction inside, outside, and below the coiled continuous body.
Figure 3C:
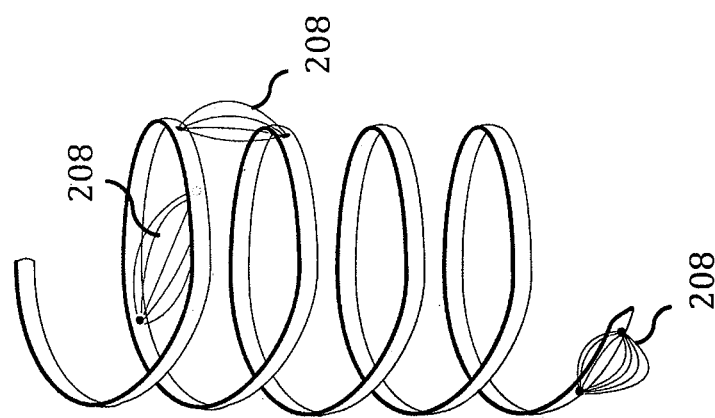
FIG. 3C shows an isometric view of microfilaments within a continuous body of a coiled shape with the end sites of the microfilaments positioned and coordinated to create the desired current characteristic at points of interaction inside, outside, and below the coiled continuous body.

FIG. 3B illustrates the six degrees of freedom possible for microfilament sites 140 within a coiled continuous body 120. These degrees of freedom of site 140 include, for example, translation along, and extension and/or retraction from the surface of continuous body 120. They also include rotation of site 140 such that it can be oriented to point in the desired direction or be located at the desired position on the surface (e.g., on top or internal surface of the continuous body). FIG. 3C shows embodiments of microfilament site 140 positioning to generate charge region 208 within, below, and outside of the continuous body. Although not shown, positioning and coordination of microfilament sites 140 to generate charge region 208 can be similar to the interaction methods described in FIG. 2. FIG. 3D shows a helical shaped continuous body 120 with waves of light 150 generated by microfilament sites 140 interfering with one another within areas 155. In some embodiments, the areas of light interference 155 can be used to increase the light intensity beyond the threshold required to modulate transfected tissue using optogenetic techniques. In other embodiments, combining different colors of light generated at sites 140 can create desired colors within areas of light interference 155. Areas of light interference 155 create controllable volumes of tissue modulation dependent upon the intensity of the light sources, colors of light sources, positioning of microfilament sites 140, focal characteristics of light sources, and frequency of light generation.

FIG. 3E shows a coiled continuous body 120 compressing and expanding with the deformation of the neural tissue 160 it is implanted within.

Figure 3F:
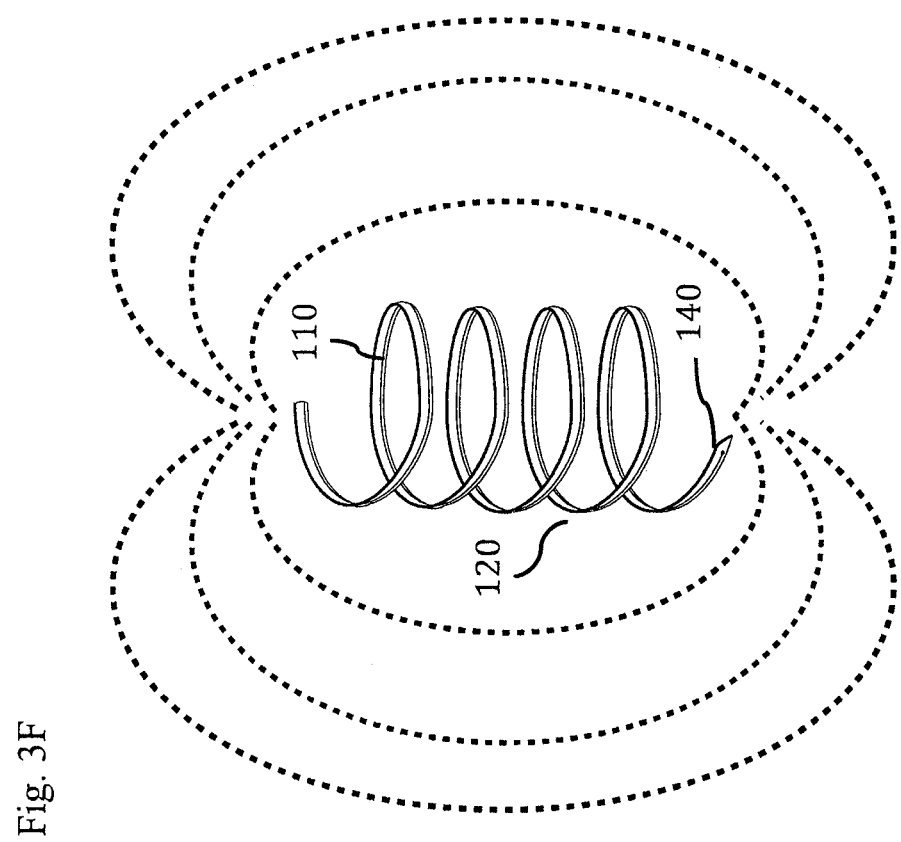
FIG. 3F illustrates an isometric view of a helical continuous body with an embedded conductive microfilament generating a magnetic field.
Figure 3G:
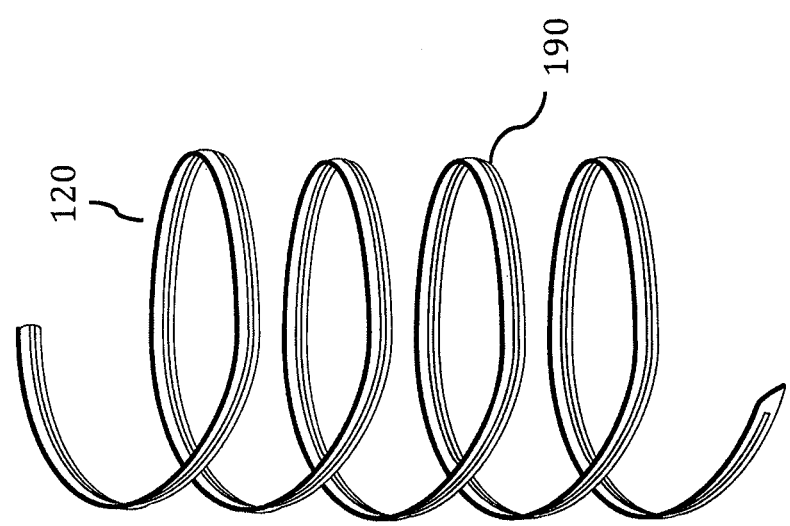
FIG. 3G shows an isometric view of a helical continuous body with an embedded tube circulating a fluid to heat or cool the surrounding tissue.

FIG. 3F illustrates a conductive microfilament 110 within a coiled continuous body 120 with a microfilament site 140 near the tip. Current passing through the microfilament generates a magnetic field 180 that stimulates surrounding tissue. In this embodiment, the current is also discharged into the tissue at the microfilament site 140. FIG. 3G shows a coiled continuous body 120 containing a hollow tube microfilament 190 therein that circulates a media, such as a fluid within the continuous body to cool or heat surrounding tissue.

Figure 3H:
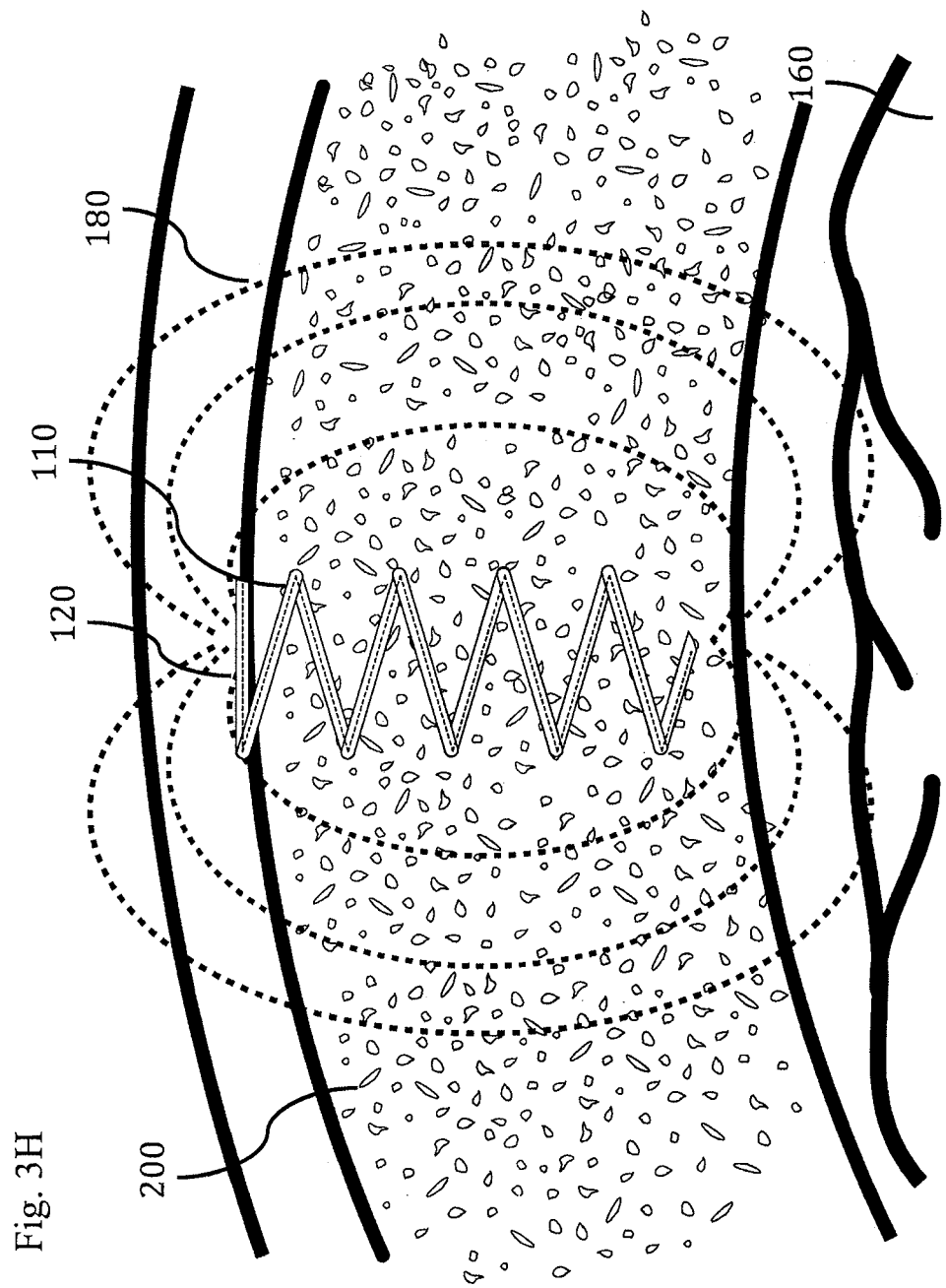
FIG. 3H shows how a coiled continuous body with an embedded conductive microfilament placed within a section of bone generating a magnetic field.

FIG. 3H shows how a coiled continuous body 120 containing a conductive microfilament 110 can also be placed within a section of bone 200 to generate a magnetic field 180 that stimulates nearby neural tissue. An external site completes the current path with the current flowing through the bone. FIG. 3I shows how a coiled continuous body 120 with an embedded optical fiber microfilament placed within a section of bone 200 generates light through a thin section of bone. In some embodiments, the bone 200 is shaped near the microfilament site before the body 120 is placed in position. Shining light through the bone can in some cases modulate the nearby neural tissue 160 using optogenetic techniques.

Figure 3J:
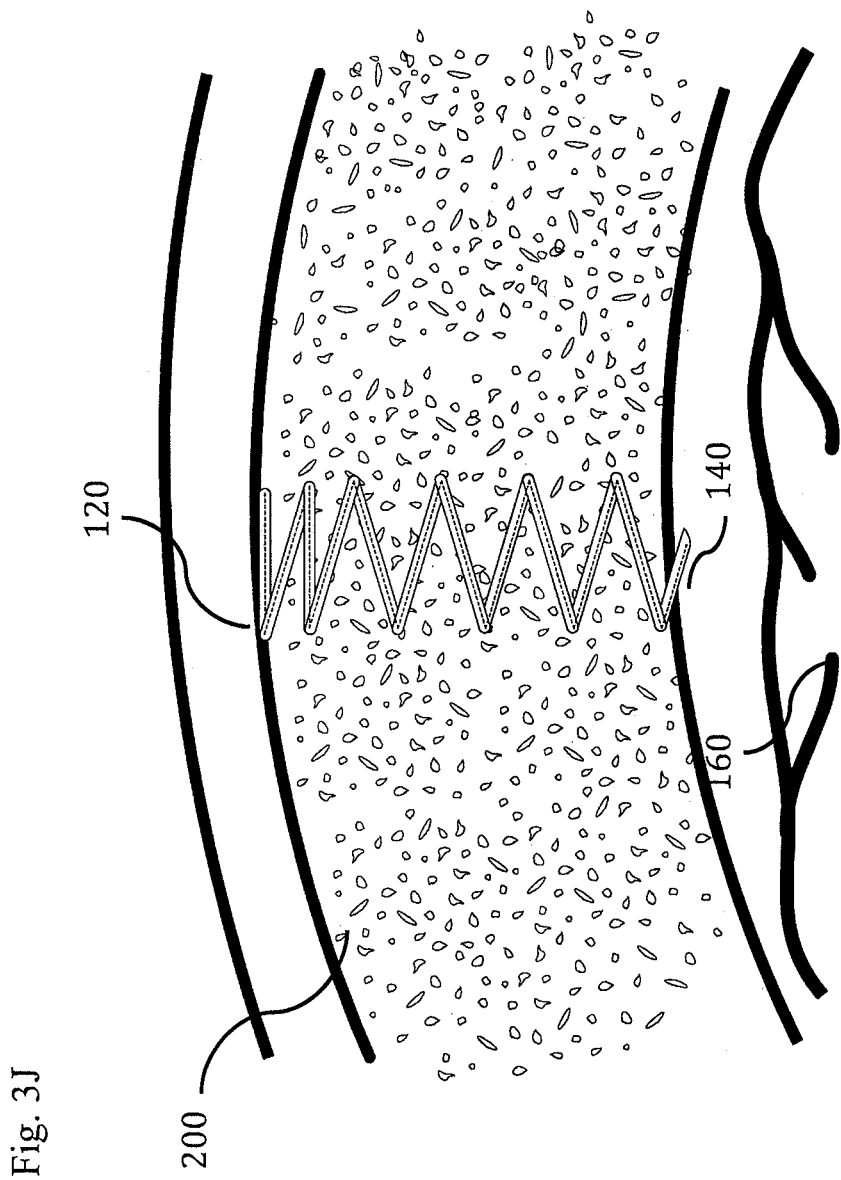
FIG. 3J illustrates a coiled continuous body containing a microfilament site near its tip that has penetrated a section of bone.

FIG. 3J illustrates a coiled continuous body 120 containing a site 140 near its distal tip that has penetrated a section of bone 200 to be proximate neural tissue. In some embodiments, a conductive microfilament site 140 can stimulate or record nearby neural tissue 160. In another embodiment, an optical fiber microfilament site 140 can stimulate nearby neural tissue using optogenetic techniques (i.e., transfection of tissue to respond to exposure to a specific form of light).

FIG. 4 shows a dense packing of microfilament sites 140 within a continuous body 120. FIG. 4A illustrates groupings 300 of a plurality of the microfilament sites 140 that provide customized recording or stimulation dependent upon specific neural tissue requirements. The groupings 300 provide a more precise, customizable, and responsive interaction with neural tissue than standard pre-shaped circular sites. The sites 140 can be configured to be linked together electrically or optically, such as via a controller for example, such that each grouping 300 functions as a single site. In some embodiments, such configurations could advantageously allow for customized site shapes that could stimulate along a specific target area of the brain; fine control over site location since the grouping 300 can be moved by one unit in all directions; or dynamic movement or a change/reassignment in identification within a particular grouping via a controller in real time to follow an area of interest (e.g., migrating the grouping such that a first microfilament is part of the first subgroup at a first point in time, but at a second point in time, the first microfilament is no longer part of the first subgroup, and a second microfilament becomes part of the first subgroup. To pack microfilament sites 140 more tightly together, in some embodiments, microfilament cross sections 110 can have varying cross sections including different circular sizes as well as rectilinear and triangular. In any embodiments disclosed herein, the array of microfilaments could include one, two, or more different types of microfilaments, e.g., electrically active, optically active, magnetically active, hollow tube microfilaments, and the like. FIG. 4B shows an embodiment of these sites packed within an area of the body or housing to reduce the non-conducting area or free space between microfilaments/electrodes to less than about 10%, 5%, 2%, 1%, or less, or between about 1-10% of the total device area. In some embodiments, it is advantageous to link recording microfilament sites 140 before amplification. These site shapes can also be created using lithographic manufacturing as well as other processes understood by those knowledgeable within the state of the art. In some embodiments, a system could include a processing unit or other features as described, for example, in U.S. Pat. No. 7,212,851 to Donoghue et al., hereby incorporated by reference in its entirety.

An embodiment of a neural microarray insertion and removal tool and method will now be described. FIG. 5 illustrates an insertion holder 500 with stem 510 above a continuous body 120 with embedded microfilaments and an opening 125. FIG. 5A shows an insertion holder 500 engaging its stem 510 with a corresponding opening 125 and driving the continuous body 120 into neural tissue 160. FIG. 5B shows the insertion holder 500 retracting its stem 510 from the opening 125. FIG. 5C illustrates the insertion holder 500 disengaging and withdrawing from contact with the continuous body 120. In some embodiments, the engagement/disengagement mechanism could include threads, a friction fit surface, a lock, movable jaws, electromagnets, or the like. A reverse process can be used such that the tool is configured to remove the continuous body from tissue once stimulation or recording is no longer required.

FIG. 6 illustrates some embodiments of continuous body 120 penetrating section tip geometry 129. Rounded outer surface 300 joining with tip is between approximately 5 μm and 400 μm, with the width between 5 μm and 200 μm. FIG. 6A illustrates concavity 301, which is between a radius of 2.0 µm and 1000 µm. FIG. 6B. illustrates rounded tip 302, which has an approximate radius between 0.1 µm and 125 µm. FIG. 6C illustrates thread 303, which is advantageous in some embodiments as it provides initial penetration of outer tissue coverings (e.g., dura) preceding a linear insertion; it can have, in some embodiments, an outer diameter between 10 µm and 200 µm, and a thread pitch between 3.0 µm and 100 µm. FIG. 6D illustrates double concavity 304, with each having a radius of curvature of approximately 2.0 µm to 1000 µm.

Although certain embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above. For all of the embodiments described above, the steps of any methods need not be performed sequentially.

What is claimed is:

1. A method of inserting a micro-scale device into a target substrate, comprising:
    providing an insertion tool comprising a housing comprising a central lumen, wherein the insertion tool further comprises a stem configured to be advanced and retracted relative to the shaft;
    mechanically coupling the stem of the insertion tool to the micro-scale device by inserting the stem into an opening of the micro-scale device;
    positioning the micro-scale device at a desired location within a target substrate;
    mechanically decoupling the stem of the insertion tool from the micro-scale device by removing the stem from the opening of the micro-scale device; and
    withdrawing the insertion tool.

2. The method of claim 1, wherein mechanically coupling the stem comprises moving the stem distally with respect to the housing of the insertion tool.

3. The method of claim 2, wherein the housing comprises a tubular body comprising the central lumen.

4. The method of claim 1, wherein mechanically coupling the stem to the micro-scale device does not substantially displace the micro-scale device.

5. The method of claim 1, further comprising monitoring the motion of the target surface.

6. The method of claim 1, wherein the micro-scale device comprises a continuous body with embedded microfilaments and the opening.

7. The method of claim 1, further comprising driving the micro-scale device in neural tissue.

8. The method of claim 1, wherein mechanically decoupling further comprises disengaging a friction fit surface.

9. The method of claim 1, wherein mechanically decoupling further comprises disengaging electromagnets.

10. The method of claim 1, wherein the micro-scale device comprises a neural microarray.

11. The method of claim 1, wherein the micro-scale device stimulates tissue or records a tissue parameter.

12. The method of claim 1, further comprising removing the micro-scale device from the target substrate.

13. A method of inserting a micro-scale device into a target substrate, comprising:
    providing an insertion tool comprising a tether having a proximal end, a distal end, and an elongate body, and an end effector operably connected to the distal end of the tether;
    mechanically coupling the end effector to a portion of the micro-scale device,;
    positioning the micro-scale device at a desired location within a target substrate;
    mechanically decoupling the end effector from the micro-scale device, wherein mechanically decoupling further comprises disengaging threads; and
    withdrawing the insertion tool.

14. The method of claim 13, wherein the micro-scale device stimulates tissue or records a tissue parameter.

15. The method of claim 13, further comprising monitoring the motion of the target surface.

16. The method of claim 13, wherein the micro-scale device comprises a continuous body with embedded microfilaments.

17. A method of inserting a micro-scale device into a target substrate, comprising:
    providing an insertion tool comprising a tether having a proximal end, a distal end, and an elongate body, and an end effector operably connected to the distal end of the tether;
    mechanically coupling the end effector to a portion of the micro-scale device, wherein the micro-scale device comprises an opening configured to receive the end effector;
    positioning the micro-scale device at a desired location within a target substrate;
    mechanically decoupling the end effector from the micro-scale device; and
    withdrawing the insertion tool.

18. The method of claim 17, wherein the micro-scale device stimulates tissue or records a tissue parameter.

19. The method of claim 17, further comprising monitoring the motion of the target surface.

20. The method of claim 17, wherein the micro-scale device comprises a continuous body with embedded microfilaments.

* * * * *